Figure 4A:
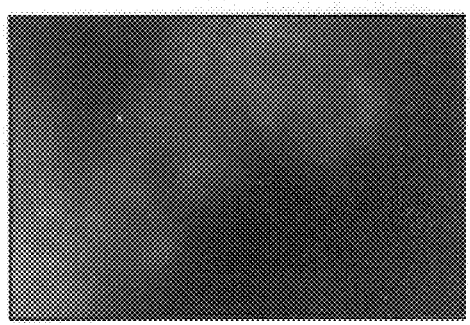

United States Patent [19]

Fu et al.

[11] Patent Number: 6,017,535
[45] Date of Patent: Jan. 25, 2000

[54] CDNA SEQUENCE OF DENGUE VIRUS SEROTYPE 1 (SINGAPORE STRAIN)

[75] Inventors: Jianlin Fu; Boon-Huan Tan; Eu-Hian Yap; Yow-Cheong Chan; Yin-Hwee Tan, all of Singapore, Singapore

[73] Assignee: Insititute of Molecular and Cell Biology, Singapore

[21] Appl. No.: 08/325,426

[22] PCT Filed: Apr. 28, 1993

[86] PCT No.: PCT/CA93/00182

§ 371 Date: Dec. 16, 1994

§ 102(e) Date: Dec. 16, 1994

[87] PCT Pub. No.: WO93/22440

PCT Pub. Date: Nov. 11, 1993

[30] Foreign Application Priority Data

Apr. 29, 1992 [GB] United Kingdom .................... 9209243

[51] Int. Cl.⁷ .......................... C12N 15/40; A61K 39/12; C07K 14/18; C07K 16/10; C12Q 1/70
[52] U.S. Cl. .................... 424/186.1; 424/218.1; 435/5; 435/69.1; 435/69.3; 435/69.7; 435/252.3; 435/252.33; 435/254.2; 435/325; 435/348; 435/320.1; 435/235.1; 536/23.72; 530/324; 530/350; 530/387.9
[58] Field of Search .............................. 424/218.1, 186.1; 435/7.1, 69.3, 320.1, 240.1, 235.1, 236, 5, 69.1, 69.7, 252.3, 252.33, 254.2, 325, 348; 530/350, 389.4, 324, 387.9; 536/23.72

[56] References Cited

PUBLICATIONS

Fu et al, "Full–Length cDNA Sequence of Dengue Type 1 Virus (Singapore Strain S275/90)", Virology 188:953–958 (1992).
Rico–Hesse, "Molecular Evolution and Distribution of Dengue Viruses Type 1 and 2 in Nature", Virology 174:479–493 (1990).
Lal et al, "Cloning Full–Length DNA Sequences of the Dneue Virus Genome for Use in Elucidating Pathogenesis and Development of Immunoprophylaxis", Vaccines, pp. 393–399 (1988).
Deubel et al, "Nucleotide Sequence and Deduced Amino Acid Sequence of the Nonstructural Proteins of Dengue Type 2 Virus, Jamaica Genotype: Comparative Analysis of the Full–Length Genome", Virology 165:234–244 (1988).
Osatomi et al, "Complete Nucleotide Sequence of Dengue Type 3 Virus Genome RNA", Virology 176:643–647 (1990).
Zhao et al, "Cloning Full–Length Dengue Type 4 Viral DNA Sequences: Analysis of Genes Coding for Structural Proteins", Virology 155:77–88 (1986).
Mason et al, "Sequence of the Dengue–1 Virus Genome in the REgion Encoding the Three Structural Proteins and the Major Nonstructural Protein NS1", Virology 161:262–267 (1987).
Westaway et al, "Flaviviridae", Intervirology 24:183–192 (1985).

Rosen, "The Pathogenesis of denuge haemorrhagic fever", Supplement to S. Afr. J. Med. 11:40–42 (1986).
Halstead, "Pathogenesis of Dengue: Challenges to Molecular Biology", Science 239:476–481 (1988).
Brinton and Dispoto, "Sequence and Secondary Structure Analysis of the 5'–Terminal Region of Flavivirus Genome RNA", Virology 162:290–299 (1988).
Irie et al, "Sequence analysis of cloned dengue virus type 2 genome (New Guinea–C strain)", Gene 75:197–211 (1989).
Wilbur and Lipman, "Rapid similarity searches of nucleic acid and protein data banks", Proc. Natl. Acad. Sci. USA 80:726–730 (1983).
Rice et al, "Nucleotide Sequence of Yellow Fever Virus: Implications for Flavivirus Gene Expression and Evolution", Science 229:726–733 (1985).
Chu et al, "Genetic Relatedness among Structural Protein Genes of Dengue 1 Virus Strains", J. Gen. Virol. 70:1701–1712 (1989).
Guan and Dixon, "Eukaryotic Proteins Expressed in *Escherichia coli*: An Improved Thrombin Cleavaged and Purification Procedure of Fusion Proteins with Glutathione S–Transferase", Anal. Biochem. 192:262–267 (1991).
Ford et al, "Fusion Tails for the Recovery and Purification of Recombinant Protiens", Prot. Exp. Pur. 2:96–107 (1991).
Maina et al, "An *Escherichia coli* vector to express and purify foreign proteins by fusion to and separation from maltose–binding protein", Gene 74:365–373 (1988).
di Guan et al, "Vectors that facilitate the expression and purification of foreign peptides in *Escherichia coli* by fusion to maltose–binding protein", Gene 67:21–30 (1991).
Zhang et al., Journal of Virology 62:3027–3031 "Immunization of mice with dengue structural proteins and nonstructural protein NS1 expressed by baculovirus recombinant induces resistance to dengue virus encephalitis", 1988.
Henchal et al., Journal of General Virology 69:2101–2107 "Synergistic interactions of anti–NS1 monoclonal antibodies protect passively immunized mice from lethal challenge with dengue 2 virus", 1988.
Hayes et al., Pediatric Infectious Disease Journal 11:311–317, "Dengue and dengue hemorrhagic fever", (Abstract Only), 1992.
Suggs et al. "Use of Synthetic oligonucleotides as hybridization probes: Isolation of cloned cDNA for human beta–2 microglobulin". PNAS. vol. 87, No. 11, pp. 6613–6617, Nov. 1981.
Doraisingham, S. "Dengue Virus Infection". Singapore Medical Journal. No. 30:523–524, 1989.

*Primary Examiner*—Mary E. Mosher
*Attorney, Agent, or Firm*—Nixon & VanderhyeP.C.

[57] ABSTRACT

DENI-S275/90 (ECACC V92042111) is a new strain of Dengue virus serotype 1. The complete cDNA sequence of this virus has been cloned and protein-coding fragments thereof have been used in the construction of expression plasmids. DEN1-S275/90 in inactivated form, DEN1-S275/90 polypeptides or fusion proteins thereof can be incorporated into vaccines for immunisation against DEN1-S275/90 and other DEN1 viruses. The invention further provides diagnostic reagents e.g. labelled antibodies to DEN1-S275/90 proteins, and kits to detect DEN1 virus.

21 Claims, 4 Drawing Sheets

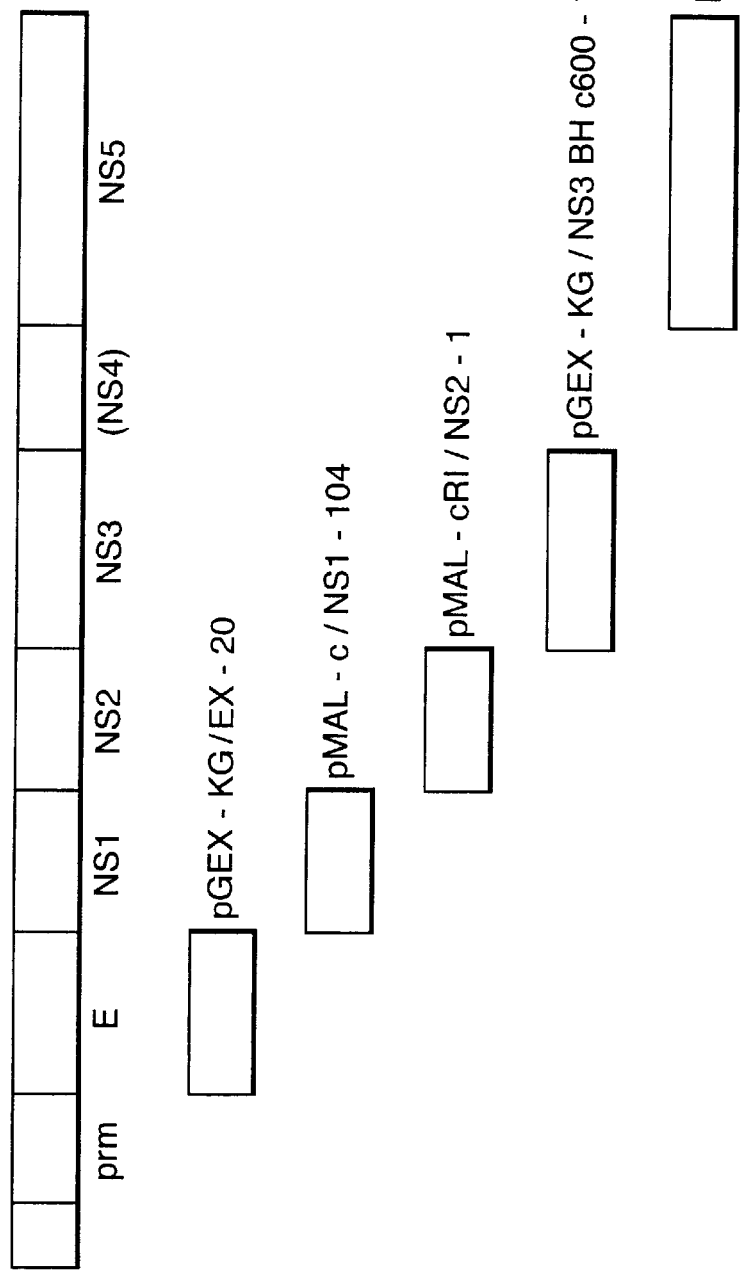

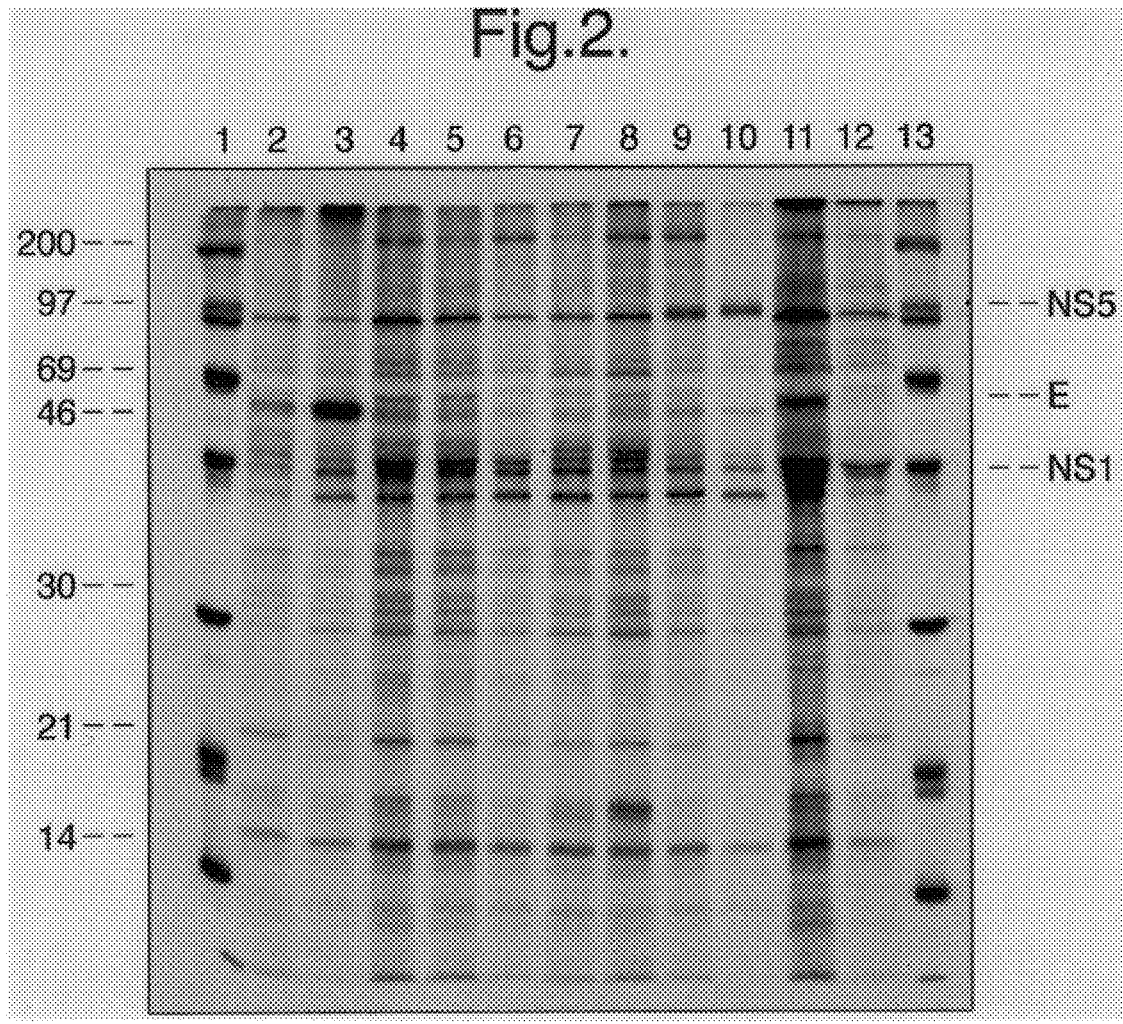

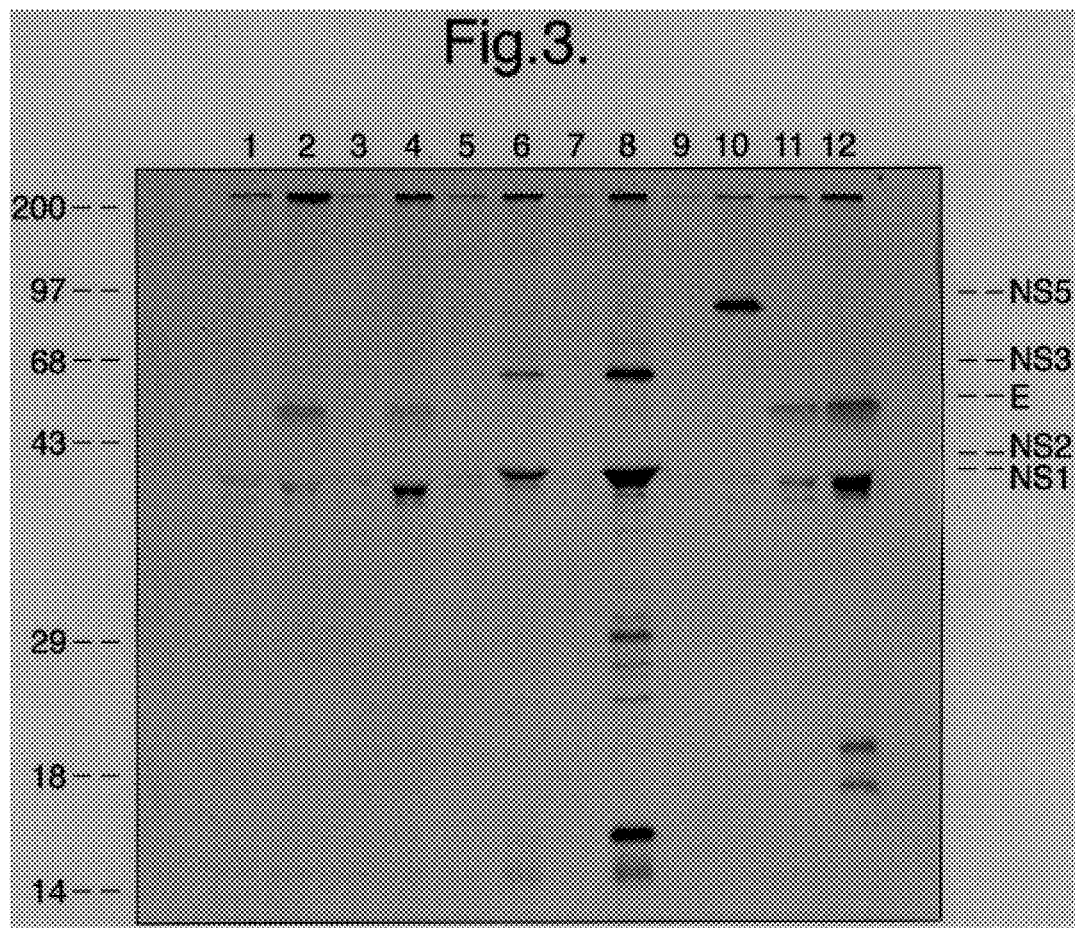

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 10718 base pairs
      (B) TYPE: nucleic acid
      (C) STRANDEDNESS: single
      (D) TOPOLOGY: linear (ii) MOLECULE TYPE: cDNA sequence corresponding to
       the genomic RNA of DEN1-S275/90

(iii) HYPOTHETICAL: NO (iv) ANTI-SENSE: NO (vi) ORIGINAL SOURCE:
      (A) ORGANISM: Dengue Fever Virus Type 1
      (B) STRAIN: S275/90

(ix) FEATURE:
      (A) NAME/KEY: CDS
      (B) LOCATION: 81..10268

(xi) SEQUENCE DESCRIPTION: SEQ ID NO:1:

```
GTGGACCGCA AAGAACAGTT TCGAATCGGA AGCTTGCTTA ACGTAGTTCT AACAGTTTTT      60

TATTAGAGAG CAGATCTCTG ATG AAC AAC CAA CGA AAA AAG ACG GCT CGA        110
                     Met Asn Asn Gln Arg Lys Lys Thr Ala Arg
                      1               5                  10

CCG TCT TTC AAT ATG CTG AAA CGC GCG AGA AAC CGC GTG TCA ACT GGT      158
Pro Ser Phe Asn Met Leu Lys Arg Ala Arg Asn Arg Val Ser Thr Gly
            15                  20                  25

TCA CAG TTG GCG AAG AGA TTC TCA AAA GGA TTG CTT TCA GGC CAA GGA      206
Ser Gln Leu Ala Lys Arg Phe Ser Lys Gly Leu Leu Ser Gly Gln Gly
        30                  35                  40

CCC ATG AAA TTG GTG ATG GCT TTC ATA GCA TTC CTA AGA TTT CTA GCC      254
Pro Met Lys Leu Val Met Ala Phe Ile Ala Phe Leu Arg Phe Leu Ala
    45                  50                  55

ATA CCC CCA ACA GCA GGA ATT TTG GCT AGA TGG GGC TCA TTC AAG AAG      302
Ile Pro Pro Thr Ala Gly Ile Leu Ala Arg Trp Gly Ser Phe Lys Lys
60                  65                  70

AAT GGA GCG ATC AAA GTG CTA CGG GGT TTC AAG AAA GAA ATC TCA AAC      350
Asn Gly Ala Ile Lys Val Leu Arg Gly Phe Lys Lys Glu Ile Ser Asn
75                  80                  85                  90

ATG TTG AAC ATA ATG AAT AGA AGG AAA AGA TCT GTG ACC ATG CTC CTC      398
Met Leu Asn Ile Met Asn Arg Arg Lys Arg Ser Val Thr Met Leu Leu
                95                  100                 105
```

-continued

| | | |
|---|---|---|
| ATG CTG CTG CCC ACA GCC TTG GCG TTC CAT TTG ACT ACA CGA GGG GGA<br>Met Leu Leu Pro Thr Ala Leu Ala Phe His Leu Thr Thr Arg Gly Gly<br>110                        115                        120 | 446 |
| GAG CCA CAC ATG ATA GTT AGC AAG CAG GAA AGA GAA AAG TCA CTC TTG<br>Glu Pro His Met Ile Val Ser Lys Gln Glu Arg Glu Lys Ser Leu Leu<br>         125                        130                        135 | 494 |
| TTT AAG ACC TCT GTA GGT GTC AAC ATG TGC ACC CTT ATA GCG ATG GAT<br>Phe Lys Thr Ser Val Gly Val Asn Met Cys Thr Leu Ile Ala Met Asp<br>140                        145                        150 | 542 |
| TTG GGA GAG TTA TGT GAG GAC ACA ATG ACT TAC AAA TGC CCT CGA ATT<br>Leu Gly Glu Leu Cys Glu Asp Thr Met Thr Tyr Lys Cys Pro Arg Ile<br>155                        160                        165                        170 | 590 |
| ACT GAG GCG GAA CCA GAT GAC GTT GAT TGT TGG TGC AAT GCT ACA GAC<br>Thr Glu Ala Glu Pro Asp Asp Val Asp Cys Trp Cys Asn Ala Thr Asp<br>                  175                        180                        185 | 638 |
| ACA TGG GTG ACC TAT GGA ACA TGT TCC CAA ACT GGC GAG CAC CGA CGG<br>Thr Trp Val Thr Tyr Gly Thr Cys Ser Gln Thr Gly Glu His Arg Arg<br>                  190                        195                        200 | 686 |
| GAC AAA CGT TCC GTC GCA CTG GCC CCA CAC GTG GGA CTT GGT CTA GAA<br>Asp Lys Arg Ser Val Ala Leu Ala Pro His Val Gly Leu Gly Leu Glu<br>         205                        210                        215 | 734 |
| ACA AGA ACC GAA ACG TGG ATG TCC TCT GAA GGC GCT TGG AAA CAA ATA<br>Thr Arg Thr Glu Thr Trp Met Ser Ser Glu Gly Ala Trp Lys Gln Ile<br>220                        225                        230 | 782 |
| CAA AGA GTG GAG ACT TGG GCT TTG CGA CAC CCA GGA TTC ACG GTG ATA<br>Gln Arg Val Glu Thr Trp Ala Leu Arg His Pro Gly Phe Thr Val Ile<br>235                        240                        245                        250 | 830 |
| GCC CTT TTT CTT GCA CAT GCC ATA GGA ACA TCC ATC ACT CAG AAA GGG<br>Ala Leu Phe Leu Ala His Ala Ile Gly Thr Ser Ile Thr Gln Lys Gly<br>                  255                        260                        265 | 878 |
| ATT ATT TTC ATT TTG TTA ATG CTA GTA ACA CCA TCC ATG GCC ATG CGA<br>Ile Ile Phe Ile Leu Leu Met Leu Val Thr Pro Ser Met Ala Met Arg<br>                  270                        275                        280 | 926 |
| TGC GTG GGA ATA GGC AGC AGG GAC TTC GTG GAA GGA CTA TCA GGA GCA<br>Cys Val Gly Ile Gly Ser Arg Asp Phe Val Glu Gly Leu Ser Gly Ala<br>                  285                        290                        295 | 974 |
| ACT TGG GTA GAC GTG GTA CTG GAA CAT GGA AGT TGC GTC ACC ACC ATG<br>Thr Trp Val Asp Val Val Leu Glu His Gly Ser Cys Val Thr Thr Met<br>300                        305                        310 | 1022 |
| GCA AAA GAC AAA CCA ACA TTG GAC ATT GAA CTC CTG AAA ACG GAG GTC<br>Ala Lys Asp Lys Pro Thr Leu Asp Ile Glu Leu Leu Lys Thr Glu Val<br>315                        320                        325                        330 | 1070 |
| ACG AAC CCT GCC GTC CTG CGC AAA CTG TGC ATT GAA GCT AAA ATA TCA<br>Thr Asn Pro Ala Val Leu Arg Lys Leu Cys Ile Glu Ala Lys Ile Ser<br>                  335                        340                        345 | 1118 |
| AAC ACC ACC ACC GAT TCA AGA TGT CCA ACA CAA GGA GAA GCT ACA CTG<br>Asn Thr Thr Thr Asp Ser Arg Cys Pro Thr Gln Gly Glu Ala Thr Leu<br>                  350                        355                        360 | 1166 |
| GTG GAA GAA CAA GAC GCG AAC TTT GTG TGT CGA CGA ACG TTC GTG GAC<br>Val Glu Glu Gln Asp Ala Asn Phe Val Cys Arg Arg Thr Phe Val Asp<br>         365                        370                        375 | 1214 |
| AGA GGC TGG GGT AAT GGC TGC GGA CTA TTT GGA AAA GGA AGC CTA CTG<br>Arg Gly Trp Gly Asn Gly Cys Gly Leu Phe Gly Lys Gly Ser Leu Leu<br>380                        385                        390 | 1262 |
| ACG TGT GCT AAG TTC AAG TGT GTG ACA AAA CTA GAA GGA AAG ATA GTT<br>Thr Cys Ala Lys Phe Lys Cys Val Thr Lys Leu Glu Gly Lys Ile Val<br>395                        400                        405                        410 | 1310 |
| CAA TAT GAA AAC TTA AAA TAT TCA GTG ATA GTC ACT GTC CAC ACT GGG<br>Gln Tyr Glu Asn Leu Lys Tyr Ser Val Ile Val Thr Val His Thr Gly<br>                  415                        420                        425 | 1358 |

```
GAC CAG CAC CAG GTG GGA AAC GAG ACT ACA GAA CAT GGA ACA ATT GCA     1406
Asp Gln His Gln Val Gly Asn Glu Thr Thr Glu His Gly Thr Ile Ala
            430                     435                 440

ACC ATA ACA CCT CAA GCT CCT ACG TCG GAA ATA CAG CTG ACC GAC TAC     1454
Thr Ile Thr Pro Gln Ala Pro Thr Ser Glu Ile Gln Leu Thr Asp Tyr
            445                     450                 455

GGA GCC CTC ACA TTG GAC TGC TCA CCT AGA ACT GGG CTG GAC TTT AAT     1502
Gly Ala Leu Thr Leu Asp Cys Ser Pro Arg Thr Gly Leu Asp Phe Asn
        460                     465                 470

GAG ATG GTG CTA TTG ACA ATG AAA GAA AAA TCA TGG CTT GTT CAC AAA     1550
Glu Met Val Leu Leu Thr Met Lys Glu Lys Ser Trp Leu Val His Lys
475                     480                     485             490

CAA TGG TTT CTA GAC TTA CCA CTG CCT TGG ACT TCG GGG GCT TCA ACA     1598
Gln Trp Phe Leu Asp Leu Pro Leu Pro Trp Thr Ser Gly Ala Ser Thr
                495                     500                 505

TCC CAA GAG ACT TGG AAC AGA CAA GAT TTG CTG GTC ACA TTC AAG ACA     1646
Ser Gln Glu Thr Trp Asn Arg Gln Asp Leu Leu Val Thr Phe Lys Thr
            510                     515                 520

GCT CAT GCA AAG AAG CAG GAA GTA GTC GTA CTG GGA TCA CAG GAA GGA     1694
Ala His Ala Lys Lys Gln Glu Val Val Val Leu Gly Ser Gln Glu Gly
            525                     530                 535

GCA ATG CAC ACT GCG TTG ACT GGG GCG ACA GAA ATC CAA ACG TCT GGA     1742
Ala Met His Thr Ala Leu Thr Gly Ala Thr Glu Ile Gln Thr Ser Gly
540                     545                     550

ACG ACA ACA ATT TTT GCA GGA CAC CTG AAA TGT AGA CTA AAA ATG GAC     1790
Thr Thr Thr Ile Phe Ala Gly His Leu Lys Cys Arg Leu Lys Met Asp
555                     560                     565             570

AAA CTG ACT CTA AAA GGG ATG TCA TAT GTG ATG TGC ACA GGC TCA TTT     1838
Lys Leu Thr Leu Lys Gly Met Ser Tyr Val Met Cys Thr Gly Ser Phe
                575                     580                 585

AAG CTA GAG AAG GAA GTG GCT GAG ACC CAG CAT GGA ACT GTT TTA GTG     1886
Lys Leu Glu Lys Glu Val Ala Glu Thr Gln His Gly Thr Val Leu Val
            590                     595                 600

CAG GTT AAA TAC GAA GGA ACA GAT GCA CCA TGC AAG ATC CCC TTT TCG     1934
Gln Val Lys Tyr Glu Gly Thr Asp Ala Pro Cys Lys Ile Pro Phe Ser
            605                     610                 615

ACC CAA GAT GAG AAA GGA GTG ACC CAG AAT AGA TTG ATA ACA GCC AAT     1982
Thr Gln Asp Glu Lys Gly Val Thr Gln Asn Arg Leu Ile Thr Ala Asn
            620                     625                 630

CCT ATA GTT ACT GAC AAA GAA AAA CCA GTC AAC ATT GAG ACA GAA CCA     2030
Pro Ile Val Thr Asp Lys Glu Lys Pro Val Asn Ile Glu Thr Glu Pro
635                     640                     645             650

CCT TTT GGT GAG AGC TAC ATC GTG GTA GGG GCA GGT GAA AAA GCT TTG     2078
Pro Phe Gly Glu Ser Tyr Ile Val Val Gly Ala Gly Glu Lys Ala Leu
                655                     660                 665

AAA CAA TGC TGG TTC AAG AAA GGA AGC AGC ATA GGG AAA ATG TTC GAA     2126
Lys Gln Cys Trp Phe Lys Lys Gly Ser Ser Ile Gly Lys Met Phe Glu
            670                     675                 680

GCA ACC GCC CGA GGA GCA CGA AGG ATG GCT ATC CTG GGA GAC ACC GCA     2174
Ala Thr Ala Arg Gly Ala Arg Arg Met Ala Ile Leu Gly Asp Thr Ala
            685                     690                 695

TGG GAC TTC GGT TCT ATA GGA GGA GTG TTC ACG TCT GTG GGA AAA TTA     2222
Trp Asp Phe Gly Ser Ile Gly Gly Val Phe Thr Ser Val Gly Lys Leu
700                     705                     710

GTG CAT CAG GTT TTT GGA ACC GCA TAT GGG GTT CTG TTC AGC GGT GTT     2270
Val His Gln Val Phe Gly Thr Ala Tyr Gly Val Leu Phe Ser Gly Val
715                     720                     725             730

TCT TGG ACC ATG AAA ATA GGA ATA GGG ATT CTG CTG ACA TGG TTG GGA     2318
Ser Trp Thr Met Lys Ile Gly Ile Gly Ile Leu Leu Thr Trp Leu Gly
                735                     740                 745
```

-continued

| | | |
|---|---|---|
| TTA AAT TCA AGG AGC ACG TCA CTT TCG ATG ACG TGC ATT GCA GTT GGC<br>Leu Asn Ser Arg Ser Thr Ser Leu Ser Met Thr Cys Ile Ala Val Gly<br>     750                            755                          760 | 2366 |
| ATG GTC ACA CTG TAC CTA GGA GTC ATG GTT CAA GCG GAC TCG GGA TGT<br>Met Val Thr Leu Tyr Leu Gly Val Met Val Gln Ala Asp Ser Gly Cys<br>     765                            770                          775 | 2414 |
| GTA ATC AAC TGG AAG GGC AGA GAA CTC AAA TGT GGA AGT GGC ATT TTT<br>Val Ile Asn Trp Lys Gly Arg Glu Leu Lys Cys Gly Ser Gly Ile Phe<br>     780                            785                          790 | 2462 |
| GTC ACT AAT GAA GTC CAC ACT TGG ACA GAG CAA TAC AAA TTT CAA GCT<br>Val Thr Asn Glu Val His Thr Trp Thr Glu Gln Tyr Lys Phe Gln Ala<br>795                         800                          805                          810 | 2510 |
| GAC TCC CCA AAA AGA CTA TCA GCA GCC ATC GGA AAG GCA TGG GAG GAG<br>Asp Ser Pro Lys Arg Leu Ser Ala Ala Ile Gly Lys Ala Trp Glu Glu<br>                        815                          820                          825 | 2558 |
| GGT GTG TGT GGA ATT CGA TCA GCC ACT CGT CTC GAG AAC ATC ATG TGG<br>Gly Val Cys Gly Ile Arg Ser Ala Thr Arg Leu Glu Asn Ile Met Trp<br>                 830                          835                          840 | 2606 |
| AAG CAA ATA TCA AAT GAA CTG AAC CAC ATC TTA CTT GAA AAT GAC ATG<br>Lys Gln Ile Ser Asn Glu Leu Asn His Ile Leu Leu Glu Asn Asp Met<br>               845                          850                          855 | 2654 |
| AAA TTC ACA GTG GTT GTA GGA GAT GTT GTT GGG ATC TTG GCC CAA GGG<br>Lys Phe Thr Val Val Val Gly Asp Val Val Gly Ile Leu Ala Gln Gly<br>     860                            865                          870 | 2702 |
| AAA AAA ATG ATT AGA CCA CAA CCC ATG GAA CAC AAA TAC TCA TGG AAA<br>Lys Lys Met Ile Arg Pro Gln Pro Met Glu His Lys Tyr Ser Trp Lys<br>875                         880                          885                          890 | 2750 |
| AGC TGG GGA AAA GCC AAA ATC ATA GGA GCA GAC ATA CAG AAC ACC ACC<br>Ser Trp Gly Lys Ala Lys Ile Ile Gly Ala Asp Ile Gln Asn Thr Thr<br>                        895                          900                          905 | 2798 |
| TTC ATC ATT GAC GGC CCA GAT ACT CCA GAA TGT CCT GAT GAC CAA AGA<br>Phe Ile Ile Asp Gly Pro Asp Thr Pro Glu Cys Pro Asp Asp Gln Arg<br>               910                          915                          920 | 2846 |
| GCA TGG AAC ATT TGG GAA GTT GAG GAC TAT GGG TTC GGA ATT TTC ACG<br>Ala Trp Asn Ile Trp Glu Val Glu Asp Tyr Gly Phe Gly Ile Phe Thr<br>         925                            930                          935 | 2894 |
| ACA AAC ATA TGG TTG AAA TTG CGT GAC TCC TAC ACC CAA ATG TGT GAC<br>Thr Asn Ile Trp Leu Lys Leu Arg Asp Ser Tyr Thr Gln Met Cys Asp<br>     940                            945                          950 | 2942 |
| CAC CGG CTA ATG TCA GCT GCC ATC AAG GAC AGC AAG GCA GTC CAT GCT<br>His Arg Leu Met Ser Ala Ala Ile Lys Asp Ser Lys Ala Val His Ala<br>955                         960                          965                          970 | 2990 |
| GAT ATG GGG TAC TGG ATA GAA AGT GAA AAG AAC GAG ACC TGG AAG CTG<br>Asp Met Gly Tyr Trp Ile Glu Ser Glu Lys Asn Glu Thr Trp Lys Leu<br>                        975                          980                          985 | 3038 |
| GCA AGA GCC TCT TTC ATA GAA GTT AAA ACA TGT GTC TGG CCA AAA TCC<br>Ala Arg Ala Ser Phe Ile Glu Val Lys Thr Cys Val Trp Pro Lys Ser<br>               990                          995                         1000 | 3086 |
| CAC ACT CTA TGG AGC AAT GGA GTT CTG GAA AGT GAA ATG ATA ATT CCA<br>His Thr Leu Trp Ser Asn Gly Val Leu Glu Ser Glu Met Ile Ile Pro<br>               1005                       1010                       1015 | 3134 |
| AAG ATC TAT GGA GGA CCA ATA TCT CAG CAC AAC TAC AGA CCA GGA TAT<br>Lys Ile Tyr Gly Gly Pro Ile Ser Gln His Asn Tyr Arg Pro Gly Tyr<br>     1020                       1025                       1030 | 3182 |
| TTC ACA CAA ACG GCA GGG CCA TGG CAC CTA GGC AAG TTG GAA CTG GAT<br>Phe Thr Gln Thr Ala Gly Pro Trp His Leu Gly Lys Leu Glu Leu Asp<br>1035                     1040                     1045                   1050 | 3230 |
| TTT GAT TTG TGT GAG GGT ACC ACA GTT GTT GTG GAT GAA CAT TGT GGA<br>Phe Asp Leu Cys Glu Gly Thr Thr Val Val Val Asp Glu His Cys Gly<br>               1055                       1060                       1065 | 3278 |

```
AAT CGA GGT CCA TCT CTT AGA ACC ACA ACA GTC ACA GGA AAG ATA ATT    3326
Asn Arg Gly Pro Ser Leu Arg Thr Thr Thr Val Thr Gly Lys Ile Ile
            1070                1075                1080

CAT GAA TGG TGT TGC AGA TCT TGT ACG CTA CCA CCC TTA CGT TTC AAA    3374
His Glu Trp Cys Cys Arg Ser Cys Thr Leu Pro Pro Leu Arg Phe Lys
        1085                1090                1095

GGA GAA GAT GGA TGT TGG TAC GGT ATG GAA ATC AGA CCA GTC AAG GAA    3422
Gly Glu Asp Gly Cys Trp Tyr Gly Met Glu Ile Arg Pro Val Lys Glu
    1100                1105                1110

AAG GAA GAG AAT CTA GTC AAA TCA ATG GTC TCT GCA GGG TCA GGG GAA    3470
Lys Glu Glu Asn Leu Val Lys Ser Met Val Ser Ala Gly Ser Gly Glu
1115                1120                1125                1130

GTG GAC AGC TTT TCA CTA GGA CTG CTA TGC ATA TCA ATA ATG ATC GAA    3518
Val Asp Ser Phe Ser Leu Gly Leu Leu Cys Ile Ser Ile Met Ile Glu
            1135                1140                1145

GAG GTG ATG AGA TCC AGA TGG AGC AGA AAA ATG CTG ATG ACT GGA ACA    3566
Glu Val Met Arg Ser Arg Trp Ser Arg Lys Met Leu Met Thr Gly Thr
        1150                1155                1160

CTG GCT GTG TTC CTC CTT CTC ATA ATG GGA CAA TTG ACA TGG AAT GAT    3614
Leu Ala Val Phe Leu Leu Leu Ile Met Gly Gln Leu Thr Trp Asn Asp
    1165                1170                1175

CTG ATC AGG TTA TGC ATC ATG GTT GGA GCC AAT GCT TCA GAC AGG ATG    3662
Leu Ile Arg Leu Cys Ile Met Val Gly Ala Asn Ala Ser Asp Arg Met
    1180                1185                1190

GGG ATG GGA ACA ACG TAC CTA GCT CTG ATG GCC ACT TTT AAA ATG AGA    3710
Gly Met Gly Thr Thr Tyr Leu Ala Leu Met Ala Thr Phe Lys Met Arg
1195                1200                1205                1210

CCA ATG TTT GCT GTC GGG CTG TTG TTC CGC AGA CTA ACA TCT AGA GAA    3758
Pro Met Phe Ala Val Gly Leu Leu Phe Arg Arg Leu Thr Ser Arg Glu
            1215                1220                1225

GTT CTT CTT CTT ACA ATT GGA TTG AGT CTA GTG GCA TCT GTG GAG TTA    3806
Val Leu Leu Leu Thr Ile Gly Leu Ser Leu Val Ala Ser Val Glu Leu
        1230                1235                1240

CCA AAT TCC CTG GAG GAG CTG GGG GAT GGA CTT GCA ATG GGC ATT ATG    3854
Pro Asn Ser Leu Glu Glu Leu Gly Asp Gly Leu Ala Met Gly Ile Met
    1245                1250                1255

ATT TTA AAA TTA TTG ACT GAC TTT CAG TCA CAT CAG CTG TGG GCT ACC    3902
Ile Leu Lys Leu Leu Thr Asp Phe Gln Ser His Gln Leu Trp Ala Thr
    1260                1265                1270

TTG CTG TCC TTG ACA TTT GTC AAA ACA ACG TTT TCC TTG CAC TAT GCA    3950
Leu Leu Ser Leu Thr Phe Val Lys Thr Thr Phe Ser Leu His Tyr Ala
1275                1280                1285                1290

TGG AAG ACA ATG GCT ATG GTA CTG TCA ATT GTA TCT CTC TTC CCC TTA    3998
Trp Lys Thr Met Ala Met Val Leu Ser Ile Val Ser Leu Phe Pro Leu
            1295                1300                1305

TGC CTG TCC ACG ACC TCC CAA AAA ACA ACA TGG CTT CCG GTG CTA TTG    4046
Cys Leu Ser Thr Thr Ser Gln Lys Thr Thr Trp Leu Pro Val Leu Leu
        1310                1315                1320

GGA TCT CTT GGA TGC AAA CCA CTA ACC ATG TTT CTC ATA GCA GAA AAC    4094
Gly Ser Leu Gly Cys Lys Pro Leu Thr Met Phe Leu Ile Ala Glu Asn
    1325                1330                1335

AAA ATC TGG GGA AGG AAA AGT TGG CCC CTC AAT GAA GGA ATC ATG GCT    4142
Lys Ile Trp Gly Arg Lys Ser Trp Pro Leu Asn Glu Gly Ile Met Ala
    1340                1345                1350

GTT GGA ATA GTC AGC ATC CTA CTA AGT TCA CTC CTC AAA AAT GAT GTG    4190
Val Gly Ile Val Ser Ile Leu Leu Ser Ser Leu Leu Lys Asn Asp Val
1355                1360                1365                1370

CCG CTA GCT GGG CCA CTA ATA GCT GGA GGC ATG CTA ATA GCA TGT TAC    4238
Pro Leu Ala Gly Pro Leu Ile Ala Gly Gly Met Leu Ile Ala Cys Tyr
            1375                1380                1385
```

-continued

| | |
|---|---|
| GTT ATA TCT GGA AGC TCA GCC GAC TTA TCA CTA GAG AAA GCG GCT GAG<br>Val Ile Ser Gly Ser Ser Ala Asp Leu Ser Leu Glu Lys Ala Ala Glu<br>          1390                    1395                    1400 | 4286 |
| GTC TCC TGG GAA GAA GAA GCA GAA CAC TCT GGT GCC TCA CAC AAT ATA<br>Val Ser Trp Glu Glu Glu Ala Glu His Ser Gly Ala Ser His Asn Ile<br>      1405                    1410                    1415 | 4334 |
| TTA GTG GAG GTC CAA GAT GAT GGA ACC ATG AAG ATA AAA GAT GAA GAG<br>Leu Val Glu Val Gln Asp Asp Gly Thr Met Lys Ile Lys Asp Glu Glu<br>1420                    1425                    1430 | 4382 |
| AGA GAT GAC ACG CTA ACC ATT CTC CTT AAA GCA ACC CTG CTA GCA GTT<br>Arg Asp Asp Thr Leu Thr Ile Leu Leu Lys Ala Thr Leu Leu Ala Val<br>1435                    1440                    1445                    1450 | 4430 |
| TCA GGG GTG TAC CCA TTA TCA ATA CCA GCA ACC CTT TTT GTG TGG TAC<br>Ser Gly Val Tyr Pro Leu Ser Ile Pro Ala Thr Leu Phe Val Trp Tyr<br>                  1455                    1460                    1465 | 4478 |
| TTT TGG CAG AAA AAG AAA CAA AGA TCT GGA GTG TTA TGG GAC ACA CCT<br>Phe Trp Gln Lys Lys Lys Gln Arg Ser Gly Val Leu Trp Asp Thr Pro<br>              1470                    1475                    1480 | 4526 |
| AGC CCT CCA GAA GTG GAA AGA GCA GTC CTT GAT GAT GGT ATC TAT AGA<br>Ser Pro Pro Glu Val Glu Arg Ala Val Leu Asp Asp Gly Ile Tyr Arg<br>            1485                    1490                    1495 | 4574 |
| ATT ATG CAG AGA GGA CTG TTG GGC AGG TCC CAA GTA GGA GTG GGA GTT<br>Ile Met Gln Arg Gly Leu Leu Gly Arg Ser Gln Val Gly Val Gly Val<br>        1500                    1505                    1510 | 4622 |
| TTC CAA GAC GGC GTG TTC CAC ACA ATG TGG CAC GTC ACC AGG GGA GCT<br>Phe Gln Asp Gly Val Phe His Thr Met Trp His Val Thr Arg Gly Ala<br>1515                    1520                    1525                    1530 | 4670 |
| GTC CTT ATG TAC CAA GGG AAG AGG CTG GAA CCA AGC TGG GCC AGT GTC<br>Val Leu Met Tyr Gln Gly Lys Arg Leu Glu Pro Ser Trp Ala Ser Val<br>                  1535                    1540                    1545 | 4718 |
| AAA AAA GAC TTG ATC TCA TAT GGA GGA GGT TGG AGG TTT CAA GGA TCC<br>Lys Lys Asp Leu Ile Ser Tyr Gly Gly Gly Trp Arg Phe Gln Gly Ser<br>              1550                    1555                    1560 | 4766 |
| TGG AAC ACG GGA GAA GAA GTG CAG GTG ATT GCT GTT GAA CCA GGA AAA<br>Trp Asn Thr Gly Glu Glu Val Gln Val Ile Ala Val Glu Pro Gly Lys<br>            1565                    1570                    1575 | 4814 |
| AAC CCC AAA AAT GTA CAG ACA GCG CCG GGT ACC TTC AAG ACC CCT GAA<br>Asn Pro Lys Asn Val Gln Thr Ala Pro Gly Thr Phe Lys Thr Pro Glu<br>        1580                    1585                    1590 | 4862 |
| GGT GAA GTT GGA GCT ATT GCC CTA GAT TTT AAA CCC GGC ACA TCT GGA<br>Gly Glu Val Gly Ala Ile Ala Leu Asp Phe Lys Pro Gly Thr Ser Gly<br>1595                    1600                    1605                    1610 | 4910 |
| TCT CCC ATC GTG AAC AGA GAA GGA AAA ATA GTA GGT CTT TAT GGA AAT<br>Ser Pro Ile Val Asn Arg Glu Gly Lys Ile Val Gly Leu Tyr Gly Asn<br>                1615                    1620                    1625 | 4958 |
| GGA GTA GTG ACA ACA AGT GGA ACC TAC GTC AGT GCC ATA GCC CAA GCC<br>Gly Val Val Thr Thr Ser Gly Thr Tyr Val Ser Ala Ile Ala Gln Ala<br>            1630                    1635                    1640 | 5006 |
| AAA GCA TCA CAA GAA GGG CCC CTA CCA GAG ATT GAG GAC GAG GTG TTT<br>Lys Ala Ser Gln Glu Gly Pro Leu Pro Glu Ile Glu Asp Glu Val Phe<br>        1645                    1650                    1655 | 5054 |
| AGG AAA AGA AAC TTA ACA ATA ATG GAC CTA CAT CCA GGA TCG GGG AAA<br>Arg Lys Arg Asn Leu Thr Ile Met Asp Leu His Pro Gly Ser Gly Lys<br>            1660                    1665                    1670 | 5102 |
| ACA AGA AGA TAT CTT CCA GCC ATA GTC CGT GAG GCC ATA AGA AGG AAC<br>Thr Arg Arg Tyr Leu Pro Ala Ile Val Arg Glu Ala Ile Arg Arg Asn<br>1675                    1680                    1685                    1690 | 5150 |
| GTG CGC ACA CTA ATT TTG GCT CCC ACA AGG GTT GTC GCT TCC GAA ATG<br>Val Arg Thr Leu Ile Leu Ala Pro Thr Arg Val Val Ala Ser Glu Met<br>                1695                    1700                    1705 | 5198 |

| | | |
|---|---|---|
| GCA GAG GCG CTC AAG GGA ATG CCA ATA AGG TAC CAA ACA ACA GCA GTG<br>Ala Glu Ala Leu Lys Gly Met Pro Ile Arg Tyr Gln Thr Thr Ala Val<br>              1710                      1715                      1720 | | 5246 |
| AAG AGT GAA CAC ACA GGA AAA GAG ATA GTT GAC CTC ATG TGT CAC GCC<br>Lys Ser Glu His Thr Gly Lys Glu Ile Val Asp Leu Met Cys His Ala<br>    1725                      1730                      1735 | | 5294 |
| ACT TTC ACC ATG CGT CTC CTG TCT CCC GTG AGA GTT CCC AAT TAC AAC<br>Thr Phe Thr Met Arg Leu Leu Ser Pro Val Arg Val Pro Asn Tyr Asn<br>        1740                      1745                      1750 | | 5342 |
| ATG ATT ATC ATG GAT GAA GCA CAT TTT ACC GAT CCA GCC AGC ATA GCG<br>Met Ile Ile Met Asp Glu Ala His Phe Thr Asp Pro Ala Ser Ile Ala<br>1755                      1760                      1765                      1770 | | 5390 |
| CGC AGA GGG TAC ATC TCA ACC CGA GTG GGC ATG GGT GAA GCA GCT GCG<br>Arg Arg Gly Tyr Ile Ser Thr Arg Val Gly Met Gly Glu Ala Ala Ala<br>                      1775                      1780                      1785 | | 5438 |
| ATC TTC ATG ACA GCC ACT CCC CCA GGA TCG GTG GAG GCC TTT CCA CAG<br>Ile Phe Met Thr Ala Thr Pro Pro Gly Ser Val Glu Ala Phe Pro Gln<br>        1790                      1795                      1800 | | 5486 |
| AGC AAT GCA GTT ATC CAA GAT GAG GAA AGA GAC ATT CCT GAG AGA TCA<br>Ser Asn Ala Val Ile Gln Asp Glu Glu Arg Asp Ile Pro Glu Arg Ser<br>              1805                      1810                      1815 | | 5534 |
| TGG AAC TCA GGC TAT GAG TGG ATC ACT GAC TTC CCA GGT AAA ACA GTC<br>Trp Asn Ser Gly Tyr Glu Trp Ile Thr Asp Phe Pro Gly Lys Thr Val<br>    1820                      1825                      1830 | | 5582 |
| TGG TTT GTT CCA AGC ATC AAA TCA GGA AAT GAC ATT GCC AAC TGC TTA<br>Trp Phe Val Pro Ser Ile Lys Ser Gly Asn Asp Ile Ala Asn Cys Leu<br>1835                      1840                      1845                      1850 | | 5630 |
| AGA AAG AAT GGG AAA CGG GTG ATT CAA TTG AGC AGG AAA ACC TTT GAT<br>Arg Lys Asn Gly Lys Arg Val Ile Gln Leu Ser Arg Lys Thr Phe Asp<br>                      1855                      1860                      1865 | | 5678 |
| ACA GAG TAC CAA AAA ACA AAA AAC AAC GAC TGG GAC TAT GTC GTC ACA<br>Thr Glu Tyr Gln Lys Thr Lys Asn Asn Asp Trp Asp Tyr Val Val Thr<br>        1870                      1875                      1880 | | 5726 |
| ACA GAT ATC TCC GAA ATG GGA GCA AAC TTC CGA GCC GAC AGG GTG ATA<br>Thr Asp Ile Ser Glu Met Gly Ala Asn Phe Arg Ala Asp Arg Val Ile<br>              1885                      1890                      1895 | | 5774 |
| GAC CCA AGA CGG TGT CTG AAA CCG GTA ATA CTA AAA GAT GGT CCA GAG<br>Asp Pro Arg Arg Cys Leu Lys Pro Val Ile Leu Lys Asp Gly Pro Glu<br>    1900                      1905                      1910 | | 5822 |
| CGC GTC ATT CTA GCC GGA CCG ATG CCA GTG ACT GTG GCC AGT GCT GCC<br>Arg Val Ile Leu Ala Gly Pro Met Pro Val Thr Val Ala Ser Ala Ala<br>1915                      1920                      1925                      1930 | | 5870 |
| CAG AGG AGA GGA AGA ATT GGA AGG AAC CAA AAC AAA GAA GGT GAT CAG<br>Gln Arg Arg Gly Arg Ile Gly Arg Asn Gln Asn Lys Glu Gly Asp Gln<br>                      1935                      1940                      1945 | | 5918 |
| TAC GTT TAC ATG GGA CAG CCT TTA AAT AAT GAT GAG GAT CAC GCT CAT<br>Tyr Val Tyr Met Gly Gln Pro Leu Asn Asn Asp Glu Asp His Ala His<br>        1950                      1955                      1960 | | 5966 |
| TGG ACA GAA GCA AAA ATG CTC CTT GAC AAT ATA AAC ACA CCA GAA GGG<br>Trp Thr Glu Ala Lys Met Leu Leu Asp Asn Ile Asn Thr Pro Glu Gly<br>              1965                      1970                      1975 | | 6014 |
| ATC ATC CCA GCC CTC TTT GAG CCA GAG AGA GAA AAG AGT GCA GCA ATA<br>Ile Ile Pro Ala Leu Phe Glu Pro Glu Arg Glu Lys Ser Ala Ala Ile<br>1980                      1985                      1990 | | 6062 |
| GAC GGG GAG TAC AGA CTG CGG GGA GAA GCA AGA AAA ACG TTT GTG GAG<br>Asp Gly Glu Tyr Arg Leu Arg Gly Glu Ala Arg Lys Thr Phe Val Glu<br>1995                      2000                      2005                      2010 | | 6110 |
| CTC ATG AGA AGA GGA GAT CTA CCT GTC TGG CTA TCC TAC AAA GTT GCC<br>Leu Met Arg Arg Gly Asp Leu Pro Val Trp Leu Ser Tyr Lys Val Ala<br>                      2015                      2020                      2025 | | 6158 |

```
TCA GAA GGC TTC CAG TAC TCT GAC AGA AGA TGG TGC TTT GAC GGG GAA    6206
Ser Glu Gly Phe Gln Tyr Ser Asp Arg Arg Trp Cys Phe Asp Gly Glu
            2030                2035                2040

AGG AAC AAC CAG GTG TTG GAG GAG AAC ATG GAC GTG GAG ATG TGG ACA    6254
Arg Asn Asn Gln Val Leu Glu Glu Asn Met Asp Val Glu Met Trp Thr
        2045                2050                2055

AAA GAA GGA GAA CGA AAG AAA CTA CGA CCC CGC TGG CTG GAT GCC AGA    6302
Lys Glu Gly Glu Arg Lys Lys Leu Arg Pro Arg Trp Leu Asp Ala Arg
    2060                2065                2070

ACA TAC TCA GAC CCA CTG GCC CTG CGC GAG TTT AAA GAG TTT GCA GCA    6350
Thr Tyr Ser Asp Pro Leu Ala Leu Arg Glu Phe Lys Glu Phe Ala Ala
2075                2080                2085                2090

GGA AGA AGA AGT GTC TCA GGT GAT CTA ATA TTA GAA ATA GGG AAA CTT    6398
Gly Arg Arg Ser Val Ser Gly Asp Leu Ile Leu Glu Ile Gly Lys Leu
            2095                2100                2105

CCA CAA CAC TTG ACG CAA AGG GCC CAG AAT GCC TTG GAC AAC CTG GTT    6446
Pro Gln His Leu Thr Gln Arg Ala Gln Asn Ala Leu Asp Asn Leu Val
        2110                2115                2120

ATG TTG CAC AAC TCC GAA CAA GGA GGA AGA GCC TAC AGA CAT GCA ATG    6494
Met Leu His Asn Ser Glu Gln Gly Gly Arg Ala Tyr Arg His Ala Met
    2125                2130                2135

GAA GAA CTT CCA GAC ACC ATA GAA ACG TTG ATG CTC CTA GCT TTG ATA    6542
Glu Glu Leu Pro Asp Thr Ile Glu Thr Leu Met Leu Leu Ala Leu Ile
2140                2145                2150

GCT GTG TTA ACT GGT GGA GTG ACG CTG TTC TTC CTA TCA GGA AAG GGC    6590
Ala Val Leu Thr Gly Gly Val Thr Leu Phe Phe Leu Ser Gly Lys Gly
2155                2160                2165                2170

CTA GGG AAA ACA TCT ATT GGC CTA CTC TGC GTG ATG GCT TCA AGC GTA    6638
Leu Gly Lys Thr Ser Ile Gly Leu Leu Cys Val Met Ala Ser Ser Val
            2175                2180                2185

CTG CTA TGG ATG GCC AGC GTG GAG CCT CAT TGG ATA GCG GCC TCC ATC    6686
Leu Leu Trp Met Ala Ser Val Glu Pro His Trp Ile Ala Ala Ser Ile
        2190                2195                2200

ATA CTA GAG TTT TTC CTG ATG GTG CTG CTT ATT CCA GAG CCA GAC AGA    6734
Ile Leu Glu Phe Phe Leu Met Val Leu Leu Ile Pro Glu Pro Asp Arg
    2205                2210                2215

CAG CGC ACT CCA CAG GAC AAC CAG TTA GCA TAT GTG GTG ATA GGT TTG    6782
Gln Arg Thr Pro Gln Asp Asn Gln Leu Ala Tyr Val Val Ile Gly Leu
2220                2225                2230

TTA TTC ATG ATA CTC ACA GTG GCA GCC AAT GAG ATG GGA TTA TTG GAA    6830
Leu Phe Met Ile Leu Thr Val Ala Ala Asn Glu Met Gly Leu Leu Glu
2235                2240                2245                2250

ACC ACA AAG AAA GAC TTA GGG ATT GGC CAT GTA GCC GCC GAA AAC CAC    6878
Thr Thr Lys Lys Asp Leu Gly Ile Gly His Val Ala Ala Glu Asn His
            2255                2260                2265

CAC CAT GCT ACA ATG CTG GAC GTA GAC CTA CGT CCA GCT TCA GCC TGG    6926
His His Ala Thr Met Leu Asp Val Asp Leu Arg Pro Ala Ser Ala Trp
        2270                2275                2280

ACC CTC TAT GCA GTA GCC ACA ACA GTT ATC ACC CCC ATG ATG AGA CAC    6974
Thr Leu Tyr Ala Val Ala Thr Thr Val Ile Thr Pro Met Met Arg His
    2285                2290                2295

ACA ATT GAA AAT ACA ACG GCA AAT ATT TCC CTG ACA GCC ATT GCA AAC    7022
Thr Ile Glu Asn Thr Thr Ala Asn Ile Ser Leu Thr Ala Ile Ala Asn
2300                2305                2310

CAG GCA GCT ATA TTG ATG GGA CTT GAT AAA GGA TGG CCA ATA TCG AAG    7070
Gln Ala Ala Ile Leu Met Gly Leu Asp Lys Gly Trp Pro Ile Ser Lys
2315                2320                2325                2330

ATG GAC ATA GGA GTT CCA CTT CTC GCC TTG GGG TGC TAT TCC CAG GTG    7118
Met Asp Ile Gly Val Pro Leu Leu Ala Leu Gly Cys Tyr Ser Gln Val
            2335                2340                2345
```

-continued

| | |
|---|---|
| AAT CCA CTG ACG CTG ACA GCG GCG GTA TTG ATG CTA GTG GCT CAT TAC<br>Asn Pro Leu Thr Leu Thr Ala Ala Val Leu Met Leu Val Ala His Tyr<br>                 2350                             2355                             2360 | 7166 |
| GCC ATA ATT GGA CCT GGA CTG CAA GCA AAA GCG ACT AGA GAA GCT CAA<br>Ala Ile Ile Gly Pro Gly Leu Gln Ala Lys Ala Thr Arg Glu Ala Gln<br>         2365                             2370                           2375 | 7214 |
| AAA AGG ACA GCG GCC GGA ATA ATG AAA AAT CCA ACC GTT GAT GGA ATT<br>Lys Arg Thr Ala Ala Gly Ile Met Lys Asn Pro Thr Val Asp Gly Ile<br>2380                           2385                           2390 | 7262 |
| GTT GCA ATA GAT TTG GAC CCT GTG GTT TAT GAT GCA AAA TTT GAG AAA<br>Val Ala Ile Asp Leu Asp Pro Val Val Tyr Asp Ala Lys Phe Glu Lys<br>2395                       2400                       2405                   2410 | 7310 |
| CAA CTA GGC CAA ATA ATG TTG TTG ATA CTA TGC ACA TCA CAG ATC CTC<br>Gln Leu Gly Gln Ile Met Leu Leu Ile Leu Cys Thr Ser Gln Ile Leu<br>                 2415                           2420                         2425 | 7358 |
| TTG ATG CGG ACT ACA TGG GCC TTG TGT GAA TCC ATC ACA CTG GCC ACT<br>Leu Met Arg Thr Thr Trp Ala Leu Cys Glu Ser Ile Thr Leu Ala Thr<br>                 2430                           2435                         2440 | 7406 |
| GGA CCT CTG ACC ACG CTT TGG GAG GGA TCT CCA GGA AAA TTT TGG AAC<br>Gly Pro Leu Thr Thr Leu Trp Glu Gly Ser Pro Gly Lys Phe Trp Asn<br>        2445                           2450                         2455 | 7454 |
| ACC ACG ATA GCG GTT TCC ATG GCA AAC ATT TTC AGG GGA AGT TAT CTA<br>Thr Thr Ile Ala Val Ser Met Ala Asn Ile Phe Arg Gly Ser Tyr Leu<br>                 2460                           2465                         2470 | 7502 |
| GCA GGA GCA GGC CTG GCC TTC TCA TTA ATG AAA TCT CTA GGA GGA GGT<br>Ala Gly Ala Gly Leu Ala Phe Ser Leu Met Lys Ser Leu Gly Gly Gly<br>2475                       2480                       2485                         2490 | 7550 |
| AGG AGA GGT ACG GGA GCC AAG GGG AAA CAC TGG GAG AGA AAT GGA AAA<br>Arg Arg Gly Thr Gly Ala Lys Gly Lys His Trp Glu Arg Asn Gly Lys<br>                         2495                         2500                         2505 | 7598 |
| GAC AGA CTG AAC CAA CTG AGC AAG TCA GAA TTC AAC ACT TAC AAA AGG<br>Asp Arg Leu Asn Gln Leu Ser Lys Ser Glu Phe Asn Thr Tyr Lys Arg<br>         2510                           2515                         2520 | 7646 |
| AGT GGG ATT ATG GAA GTG GAC AGA TCC GAA GCC AAA GAG GGA CTG AAA<br>Ser Gly Ile Met Glu Val Asp Arg Ser Glu Ala Lys Glu Gly Leu Lys<br>                 2525                         2530                         2535 | 7694 |
| AGA GGA GAA ACA ACC AAA CAT GCA GTG TCG AGA GGA ACC GCC AAA TTG<br>Arg Gly Glu Thr Thr Lys His Ala Val Ser Arg Gly Thr Ala Lys Leu<br>        2540                           2545                         2550 | 7742 |
| AGG TGG TTC GTG GAG AGG AAC CTT GTG AAA CCA GAA GGG AAA GTC ATA<br>Arg Trp Phe Val Glu Arg Asn Leu Val Lys Pro Glu Gly Lys Val Ile<br>2555                       2560                       2565                         2570 | 7790 |
| GAC CTC GGT TGT GGA AGA GGT GGC TGG TCA TAC TAT TGC GCT GGG CTG<br>Asp Leu Gly Cys Gly Arg Gly Gly Trp Ser Tyr Tyr Cys Ala Gly Leu<br>                 2575                           2580                         2585 | 7838 |
| AAG AAA GTC ACA GAA GTG AAG GGA TAC ACA AAA GGA GGA CCT GGA CAT<br>Lys Lys Val Thr Glu Val Lys Gly Tyr Thr Lys Gly Gly Pro Gly His<br>                         2590                         2595                         2600 | 7886 |
| GAG GAA CCA ATC CCA ATG GCG ACC TAT GGA TGG AAC CTA GTA AAG CTA<br>Glu Glu Pro Ile Pro Met Ala Thr Tyr Gly Trp Asn Leu Val Lys Leu<br>         2605                           2610                         2615 | 7934 |
| TAC TCC GGG AAA GAC GTA TTC TTT ACA CCA CCT GAG AAG TGT GAC ACC<br>Tyr Ser Gly Lys Asp Val Phe Phe Thr Pro Pro Glu Lys Cys Asp Thr<br>                 2620                           2625                         2630 | 7982 |
| CTT TTG TGT GAT ATT GGT GAG TCC TCT CCA AAC CCA ACT ATA GAA GAA<br>Leu Leu Cys Asp Ile Gly Glu Ser Ser Pro Asn Pro Thr Ile Glu Glu<br>2635                       2640                       2645                         2650 | 8030 |
| GGA AGA ACG TTA CGC GTC CTA AAG ATG GTG GAA CCA TGG CTC AGA GGG<br>Gly Arg Thr Leu Arg Val Leu Lys Met Val Glu Pro Trp Leu Arg Gly<br>                 2655                           2660                         2665 | 8078 |

```
AAC CAA TTT TGC ATA AAA ATT CTA AAT CCC TAC ATG CCA AGT GTG GTG    8126
Asn Gln Phe Cys Ile Lys Ile Leu Asn Pro Tyr Met Pro Ser Val Val
            2670                2675                2680

GAA ACT CTG GAG CAA ATG CAA AGA AAA CAT GGA GGA ATG CTA GTG CGG    8174
Glu Thr Leu Glu Gln Met Gln Arg Lys His Gly Gly Met Leu Val Arg
    2685                2690                2695

AAT CCA CTT TCA AGA AAT TCT ACT CAT GAA ATG TAT TGG GTT TCA TGT    8222
Asn Pro Leu Ser Arg Asn Ser Thr His Glu Met Tyr Trp Val Ser Cys
        2700                2705                2710

GGA ACA GGA AAC ATT GTG TCA GCA GTA AAC ATG ACA TCT AGA ATG TTG    8270
Gly Thr Gly Asn Ile Val Ser Ala Val Asn Met Thr Ser Arg Met Leu
2715                2720                2725                2730

CTA AAT CGA TTC ACA ATG GCT CAC AGG AAA CCA ACA TAT GAA AGA GAC    8318
Leu Asn Arg Phe Thr Met Ala His Arg Lys Pro Thr Tyr Glu Arg Asp
            2735                2740                2745

GTG GAC TTA GGC GCT GGA ACA AGA CAT GTG GCA GTG GAA CCA GAG GTA    8366
Val Asp Leu Gly Ala Gly Thr Arg His Val Ala Val Glu Pro Glu Val
        2750                2755                2760

GCC AAC CTA GAT ATC ATT GGC CAG AGG ATA GAG AAC ATA AAA CAT GAA    8414
Ala Asn Leu Asp Ile Ile Gly Gln Arg Ile Glu Asn Ile Lys His Glu
    2765                2770                2775

CAT AAG TCA ACA TGG CAT TAT GAT GAG GAC AAT CCA TAT AAA ACA TGG    8462
His Lys Ser Thr Trp His Tyr Asp Glu Asp Asn Pro Tyr Lys Thr Trp
        2780                2785                2790

GCC TAT CAT GGA TCA TAT GAG GTC AAG CCA TCA GGA TCA GCC TCA TCC    8510
Ala Tyr His Gly Ser Tyr Glu Val Lys Pro Ser Gly Ser Ala Ser Ser
2795                2800                2805                2810

ATG GTC AAT GGC GTG GTG AAA CTG CTC ACC AAA CCA TGG GAT GCC ATC    8558
Met Val Asn Gly Val Val Lys Leu Leu Thr Lys Pro Trp Asp Ala Ile
            2815                2820                2825

CCC ATG GTC ACA CAA ATA GCC ATG ACT GAC ACC ACA CCC TTT GGA CAA    8606
Pro Met Val Thr Gln Ile Ala Met Thr Asp Thr Thr Pro Phe Gly Gln
        2830                2835                2840

CAG AGG GTG TTT AAA GAG AAA GTT GAC ACG CGC ACA CCA AAA GCA AAA    8654
Gln Arg Val Phe Lys Glu Lys Val Asp Thr Arg Thr Pro Lys Ala Lys
    2845                2850                2855

CGA GGC ACA GCA CAA ATC ATG GAG GTG ACA GCC AGG TGG TTA TGG GGT    8702
Arg Gly Thr Ala Gln Ile Met Glu Val Thr Ala Arg Trp Leu Trp Gly
        2860                2865                2870

TTT CTC TCT AGA AAC AAA AAA CCA AGA ATT TGT ACA AGA GAG GAG TTC    8750
Phe Leu Ser Arg Asn Lys Lys Pro Arg Ile Cys Thr Arg Glu Glu Phe
2875                2880                2885                2890

ACA AGA AAA GTT AGG TCA AAC GCA GCC ATT GGA GCA GTG TTC GTT GAT    8798
Thr Arg Lys Val Arg Ser Asn Ala Ala Ile Gly Ala Val Phe Val Asp
            2895                2900                2905

GAA AAT CAA TGG AAC TCA GCA AAA GAA GCA GTG GAA GAT GAG CGG TTC    8846
Glu Asn Gln Trp Asn Ser Ala Lys Glu Ala Val Glu Asp Glu Arg Phe
        2910                2915                2920

TGG GAC CTT GTG CAC AGA GAG AGG GAG CTT CAC AAA CAG GGA AAA TGT    8894
Trp Asp Leu Val His Arg Glu Arg Glu Leu His Lys Gln Gly Lys Cys
    2925                2930                2935

GCC ACG TGT GTT TAC AAC ATG ATG GGG AAG AGA GAG AAA AAA CTA GGA    8942
Ala Thr Cys Val Tyr Asn Met Met Gly Lys Arg Glu Lys Lys Leu Gly
        2940                2945                2950

GAG TTC GGA AAG GCA AAA GGA AGT CGT GCA ATA TGG TAC ATG TGG TTG    8990
Glu Phe Gly Lys Ala Lys Gly Ser Arg Ala Ile Trp Tyr Met Trp Leu
2955                2960                2965                2970

GGA GCA CGC TTT CTA GAG TTC GAA GCT CTT GGT TTC ATG AAC GAA GAT    9038
Gly Ala Arg Phe Leu Glu Phe Glu Ala Leu Gly Phe Met Asn Glu Asp
            2975                2980                2985
```

-continued

| | |
|---|---|
| CAC TGG TTC AGT AGA GAG AAT TCA CTC AGT GGA GTG AAA GGA GAA GGA<br>His Trp Phe Ser Arg Glu Asn Ser Leu Ser Gly Val Glu Gly Glu Gly<br>               2990                 2995                 3000 | 9086 |
| CTC CAC AAA CTC GGA TAT ATA CTC AGA GAC ATA TCA AAG ATT CCA GGG<br>Leu His Lys Leu Gly Tyr Ile Leu Arg Asp Ile Ser Lys Ile Pro Gly<br>3005                 3010                 3015 | 9134 |
| GGA AAT ATG TAT GCA GAT GAC ACA GCC GGA TGG GAT ACA AGG ATA ACA<br>Gly Asn Met Tyr Ala Asp Asp Thr Ala Gly Trp Asp Thr Arg Ile Thr<br>               3020                 3025                 3030 | 9182 |
| GAG GAT GAT CTT CAG AAT GAG GCC AAA ATT ACT GAC ATC ATG GAG CCC<br>Glu Asp Asp Leu Gln Asn Glu Ala Lys Ile Thr Asp Ile Met Glu Pro<br>3035                 3040                 3045                 3050 | 9230 |
| GAA CAT GCC CTA CTG GCT ACG TCA ATC TTC AAG CTG ACC TAC CAA AAT<br>Glu His Ala Leu Leu Ala Thr Ser Ile Phe Lys Leu Thr Tyr Gln Asn<br>               3055                 3060                 3065 | 9278 |
| AAG GTG GTA AGG GTA CAG AGA CCA GCG AAA AAT GGA ACC GTG ATG GAT<br>Lys Val Val Arg Val Gln Arg Pro Ala Lys Asn Gly Thr Val Met Asp<br>               3070                 3075                 3080 | 9326 |
| GTC ATA TCC AGA CGT GAC CAG AGA GGA AGT GGC CAG GTC GGA ACT TAT<br>Val Ile Ser Arg Arg Asp Gln Arg Gly Ser Gly Gln Val Gly Thr Tyr<br>               3085                 3090                 3095 | 9374 |
| GGC TTA AAC ACT TTC ACT AAC ATG GAA GCC CAG CTA ATA AGA CAA ATG<br>Gly Leu Asn Thr Phe Thr Asn Met Glu Ala Gln Leu Ile Arg Gln Met<br>               3100                 3105                 3110 | 9422 |
| GAG TCT GAG GGA ATC TTT TCA CCC AGC GAA TTG GAG ACC CCA AAT TTA<br>Glu Ser Glu Gly Ile Phe Ser Pro Ser Glu Leu Glu Thr Pro Asn Leu<br>3115                 3120                 3125                 3130 | 9470 |
| GCC GAG AGA GTT CTC GAC TGG CTG GAA AAA TAT GGC GTC GAA AGG CTG<br>Ala Glu Arg Val Leu Asp Trp Leu Glu Lys Tyr Gly Val Glu Arg Leu<br>               3135                 3140                 3145 | 9518 |
| AAA AGA ATG GCA ATC AGC GGA GAT GAC TGC GTG GTG AAA CCA ATT GAT<br>Lys Arg Met Ala Ile Ser Gly Asp Asp Cys Val Val Lys Pro Ile Asp<br>               3150                 3155                 3160 | 9566 |
| GAC AGG TTC GCA ACA GCC TTA ACA GCT CTG AAT GAT ATG GGA AAA GTA<br>Asp Arg Phe Ala Thr Ala Leu Thr Ala Leu Asn Asp Met Gly Lys Val<br>               3165                 3170                 3175 | 9614 |
| AGA AAA GAT ATA CCA CAA TGG GAA CCC TCA AAA GGA TGG AAT GAT TGG<br>Arg Lys Asp Ile Pro Gln Trp Glu Pro Ser Lys Gly Trp Asn Asp Trp<br>               3180                 3185                 3190 | 9662 |
| CAA CAG GTG CCT TTT TGT TCA CAC CAT TTC CAC CAG CTG ATT ATG AAG<br>Gln Gln Val Pro Phe Cys Ser His His Phe His Gln Leu Ile Met Lys<br>3195                 3200                 3205                 3210 | 9710 |
| GAT GGG AGG GAA ATA GTG GTG CCA TGC CGC AAC CAA GAT GAA CTT GTG<br>Asp Gly Arg Glu Ile Val Val Pro Cys Arg Asn Gln Asp Glu Leu Val<br>               3215                 3220                 3225 | 9758 |
| GGT AGG GCT AGA GTA TCA CAA GGT GCT GGA TGG AGC CTG AGA GAA ACT<br>Gly Arg Ala Arg Val Ser Gln Gly Ala Gly Trp Ser Leu Arg Glu Thr<br>               3230                 3235                 3240 | 9806 |
| GCA TGC CTA GGC AAG TCA TAT GCA CAA ATG TGG CAG CTG ATG TAC TTC<br>Ala Cys Leu Gly Lys Ser Tyr Ala Gln Met Trp Gln Leu Met Tyr Phe<br>               3245                 3250                 3255 | 9854 |
| CAC AGG AGA GAC CTG AGA CTA GCT GCT AAT GCT ATC TGT TCA GCC GTT<br>His Arg Arg Asp Leu Arg Leu Ala Ala Asn Ala Ile Cys Ser Ala Val<br>               3260                 3265                 3270 | 9902 |
| CCA GTT GAT TGG GTC CCA ACC AGC CGC ACC ACT TGG TCG ATC CAT GCC<br>Pro Val Asp Trp Val Pro Thr Ser Arg Thr Thr Trp Ser Ile His Ala<br>3275                 3280                 3285                 3290 | 9950 |
| CAT CAC CAA TGG ATG ACA ACA GAA GAC ATG TTG TCA GTG TGG AAT AGG<br>His His Gln Trp Met Thr Thr Glu Asp Met Leu Ser Val Trp Asn Arg<br>               3295                 3300                 3305 | 9998 |

```
GTT TGG ATA GAG GAA AAC CCA TGG ATG GAG GAC AAA ACC CAT GTA TCC      10046
Val Trp Ile Glu Glu Asn Pro Trp Met Glu Asp Lys Thr His Val Ser
            3310                3315                3320

AGT TGG GAA GAT GTT CCA TAT TTA GGA AAA AGG GAA GAT CAG TGG TGT      10094
Ser Trp Glu Asp Val Pro Tyr Leu Gly Lys Arg Glu Asp Gln Trp Cys
        3325                3330                3335

GGA TCC CTG ATA GGC TTA ACA GCA AGG GCT ACC TGG GCC ACC AAC ATA      10142
Gly Ser Leu Ile Gly Leu Thr Ala Arg Ala Thr Trp Ala Thr Asn Ile
    3340                3345                3350

CAA GTG GCC ATA AAC CAA GTG AGA AGA CTA ATC GGG AAT GAG AAT TAT      10190
Gln Val Ala Ile Asn Gln Val Arg Arg Leu Ile Gly Asn Glu Asn Tyr
3355                3360                3365                3370

CTA GAT TAC ATG ACA TCA ATG AAG AGA TTC AAG AAC GAG AGT GAT CCG      10238
Leu Asp Tyr Met Thr Ser Met Lys Arg Phe Lys Asn Glu Ser Asp Pro
            3375                3380                3385

AAG GGG CAC TCT GGT GAG TCA ACA CAC TTA TGAAATAAA GGAAATAAG          10288
Lys Gly His Ser Gly Glu Ser Thr His Leu
        3390                3395

AAATCAAACA AGGCAAGAAG TCAGGCCGGA TTAAGCCATA GTACGGTAAG AGCTATGCTG    10348

CCTGTGAGCC CCGTCCAAGG ACGTAAAATG AAGTCAGGCC GAAAGCCACG GTTTGAGCAA    10408

ACCGTGCTGC CTGTAGCTTC ATCGTGGGGA TGTAAAAACC TGGGAGGCTG CAACCCATGG    10468

AAGCTGTACG CATGGGGTAG CAGACTAGTG GTTAGAGGAG ACCCCTCCCA AAACATAACG    10528

CAGCAGCGGG GCCCAACACC AGGGGAAGCT GTATCCTGGT GGTAAGGACT AGAGGTTAGA    10588

GGAGACCCCC GGCATAACAA TAAACAGCAT ATTGACGCTG GGAGAGACCA GAGATCCTGC    10648

TGTCTCTACA GCATCATTCC AGGCACAGAA CGCCAGAAAA TGGAATGGTG CTGTTGAATC    10708

AACAGGTTCT                                                          10718

(2) INFORMATION FOR SEQ ID NO:2:

(i) SEQUENCE CHARACTERISTICS:
        (A) LENGTH: 3396 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Asn Gln Arg Lys Lys Thr Ala Arg Pro Ser Phe Asn Met Leu
  1               5                  10                  15

Lys Arg Ala Arg Asn Arg Val Ser Thr Gly Ser Gln Leu Ala Lys Arg
             20                  25                  30

Phe Ser Lys Gly Leu Leu Ser Gly Gln Gly Pro Met Lys Leu Val Met
         35                  40                  45

Ala Phe Ile Ala Phe Leu Arg Phe Leu Ala Ile Pro Pro Thr Ala Gly
     50                  55                  60

Ile Leu Ala Arg Trp Gly Ser Phe Lys Lys Asn Gly Ala Ile Lys Val
 65                  70                  75                  80

Leu Arg Gly Phe Lys Lys Glu Ile Ser Asn Met Leu Asn Ile Met Asn
             85                  90                  95

Arg Arg Lys Arg Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Glu Lys Ser Leu Leu Phe Lys Thr Ser Val Gly
    130                 135                 140

Val Asn Met Cys Thr Leu Ile Ala Met Asp Leu Gly Glu Leu Cys Glu
```

```
                    145                 150                 155                 160
Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Thr Glu Thr Trp
    210                 215                 220

Met Ser Ser Glu Gly Ala Trp Lys Gln Ile Gln Arg Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
                260                 265                 270

Met Leu Val Thr Pro Ser Met Ala Met Arg Cys Val Gly Ile Gly Ser
            275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
                340                 345                 350

Arg Cys Pro Thr Gln Gly Glu Ala Thr Leu Val Glu Glu Gln Asp Ala
            355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Leu Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
                420                 425                 430

Asn Glu Thr Thr Glu His Gly Thr Ile Ala Thr Ile Thr Pro Gln Ala
            435                 440                 445

Pro Thr Ser Glu Ile Gln Leu Thr Asp Tyr Gly Ala Leu Thr Leu Asp
    450                 455                 460

Cys Ser Pro Arg Thr Gly Leu Asp Phe Asn Glu Met Val Leu Leu Thr
465                 470                 475                 480

Met Lys Glu Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
                500                 505                 510

Arg Gln Asp Leu Leu Val Thr Phe Lys Thr Ala His Ala Lys Lys Gln
            515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575
```

```
Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
610                     615                 620

Val Thr Gln Asn Arg Leu Ile Thr Ala Asn Pro Ile Val Thr Asp Lys
625                 630                 635                 640

Glu Lys Pro Val Asn Ile Glu Thr Glu Pro Pro Phe Gly Glu Ser Tyr
                645                 650                 655

Ile Val Val Gly Ala Gly Glu Lys Ala Leu Lys Gln Cys Trp Phe Lys
                660                 665                 670

Lys Gly Ser Ser Ile Gly Lys Met Phe Glu Ala Thr Ala Arg Gly Ala
            675                 680                 685

Arg Arg Met Ala Ile Leu Gly Asp Thr Ala Trp Asp Phe Gly Ser Ile
690                 695                 700

Gly Gly Val Phe Thr Ser Val Gly Lys Leu Val His Gln Val Phe Gly
705                 710                 715                 720

Thr Ala Tyr Gly Val Leu Phe Ser Gly Val Ser Trp Thr Met Lys Ile
                725                 730                 735

Gly Ile Gly Ile Leu Leu Thr Trp Leu Gly Leu Asn Ser Arg Ser Thr
            740                 745                 750

Ser Leu Ser Met Thr Cys Ile Ala Val Gly Met Val Thr Leu Tyr Leu
        755                 760                 765

Gly Val Met Val Gln Ala Asp Ser Gly Cys Val Ile Asn Trp Lys Gly
770                 775                 780

Arg Glu Leu Lys Cys Gly Ser Gly Ile Phe Val Thr Asn Glu Val His
785                 790                 795                 800

Thr Trp Thr Glu Gln Tyr Lys Phe Gln Ala Asp Ser Pro Lys Arg Leu
                805                 810                 815

Ser Ala Ala Ile Gly Lys Ala Trp Glu Glu Gly Val Cys Gly Ile Arg
            820                 825                 830

Ser Ala Thr Arg Leu Glu Asn Ile Met Trp Lys Gln Ile Ser Asn Glu
        835                 840                 845

Leu Asn His Ile Leu Leu Glu Asn Asp Met Lys Phe Thr Val Val Val
850                 855                 860

Gly Asp Val Val Gly Ile Leu Ala Gln Gly Lys Lys Met Ile Arg Pro
865                 870                 875                 880

Gln Pro Met Glu His Lys Tyr Ser Trp Lys Ser Trp Gly Lys Ala Lys
                885                 890                 895

Ile Ile Gly Ala Asp Ile Gln Asn Thr Thr Phe Ile Ile Asp Gly Pro
            900                 905                 910

Asp Thr Pro Glu Cys Pro Asp Asp Gln Arg Ala Trp Asn Ile Trp Glu
        915                 920                 925

Val Glu Asp Tyr Gly Phe Gly Ile Phe Thr Thr Asn Ile Trp Leu Lys
930                 935                 940

Leu Arg Asp Ser Tyr Thr Gln Met Cys Asp His Arg Leu Met Ser Ala
945                 950                 955                 960

Ala Ile Lys Asp Ser Lys Ala Val His Ala Asp Met Gly Tyr Trp Ile
                965                 970                 975

Glu Ser Glu Lys Asn Glu Thr Trp Lys Leu Ala Arg Ala Ser Phe Ile
            980                 985                 990

Glu Val Lys Thr Cys Val Trp Pro Lys Ser His Thr Leu Trp Ser Asn
        995                 1000                1005
```

```
Gly Val Leu Glu Ser Glu Met Ile Ile Pro Lys Ile Tyr Gly Gly Pro
    1010                1015                1020

Ile Ser Gln His Asn Tyr Arg Pro Gly Tyr Phe Thr Gln Thr Ala Gly
1025                1030                1035                1040

Pro Trp His Leu Gly Lys Leu Glu Leu Asp Phe Asp Leu Cys Glu Gly
                1045                1050                1055

Thr Thr Val Val Val Asp Glu His Cys Gly Asn Arg Gly Pro Ser Leu
        1060                1065                1070

Arg Thr Thr Thr Val Thr Gly Lys Ile Ile His Glu Trp Cys Cys Arg
    1075                1080                1085

Ser Cys Thr Leu Pro Pro Leu Arg Phe Lys Gly Glu Asp Gly Cys Trp
    1090                1095                1100

Tyr Gly Met Glu Ile Arg Pro Val Lys Glu Lys Glu Glu Asn Leu Val
1105                1110                1115                1120

Lys Ser Met Val Ser Ala Gly Ser Gly Glu Val Asp Ser Phe Ser Leu
                1125                1130                1135

Gly Leu Leu Cys Ile Ser Ile Met Ile Glu Glu Val Met Arg Ser Arg
            1140                1145                1150

Trp Ser Arg Lys Met Leu Met Thr Gly Thr Leu Ala Val Phe Leu Leu
        1155                1160                1165

Leu Ile Met Gly Gln Leu Thr Trp Asn Asp Leu Ile Arg Leu Cys Ile
    1170                1175                1180

Met Val Gly Ala Asn Ala Ser Asp Arg Met Gly Met Gly Thr Thr Tyr
1185                1190                1195                1200

Leu Ala Leu Met Ala Thr Phe Lys Met Arg Pro Met Phe Ala Val Gly
                1205                1210                1215

Leu Leu Phe Arg Arg Leu Thr Ser Arg Glu Val Leu Leu Leu Thr Ile
            1220                1225                1230

Gly Leu Ser Leu Val Ala Ser Val Glu Leu Pro Asn Ser Leu Glu Glu
        1235                1240                1245

Leu Gly Asp Gly Leu Ala Met Gly Ile Met Ile Leu Lys Leu Leu Thr
    1250                1255                1260

Asp Phe Gln Ser His Gln Leu Trp Ala Thr Leu Leu Ser Leu Thr Phe
1265                1270                1275                1280

Val Lys Thr Thr Phe Ser Leu His Tyr Ala Trp Lys Thr Met Ala Met
                1285                1290                1295

Val Leu Ser Ile Val Ser Leu Phe Pro Leu Cys Leu Ser Thr Thr Ser
            1300                1305                1310

Gln Lys Thr Thr Trp Leu Pro Val Leu Leu Gly Ser Leu Gly Cys Lys
        1315                1320                1325

Pro Leu Thr Met Phe Leu Ile Ala Glu Asn Lys Ile Trp Gly Arg Lys
    1330                1335                1340

Ser Trp Pro Leu Asn Glu Gly Ile Met Ala Val Gly Ile Val Ser Ile
1345                1350                1355                1360

Leu Leu Ser Ser Leu Leu Lys Asn Asp Val Pro Leu Ala Gly Pro Leu
                1365                1370                1375

Ile Ala Gly Gly Met Leu Ile Ala Cys Tyr Val Ile Ser Gly Ser Ser
            1380                1385                1390

Ala Asp Leu Ser Leu Glu Lys Ala Ala Glu Val Ser Trp Glu Glu Glu
        1395                1400                1405

Ala Glu His Ser Gly Ala Ser His Asn Ile Leu Val Glu Val Gln Asp
    1410                1415                1420

Asp Gly Thr Met Lys Ile Lys Asp Glu Glu Arg Asp Asp Thr Leu Thr
```

```
                1425              1430              1435              1440
Ile Leu Leu Lys Ala Thr Leu Ala Val Ser Gly Val Tyr Pro Leu
                     1445              1450              1455

Ser Ile Pro Ala Thr Leu Phe Val Trp Tyr Phe Trp Gln Lys Lys
         1460              1465              1470

Gln Arg Ser Gly Val Leu Trp Asp Thr Pro Ser Pro Glu Val Glu
         1475              1480              1485

Arg Ala Val Leu Asp Asp Gly Ile Tyr Arg Ile Met Gln Arg Gly Leu
         1490              1495              1500

Leu Gly Arg Ser Gln Val Gly Val Gly Val Phe Gln Asp Gly Val Phe
1505              1510              1515              1520

His Thr Met Trp His Val Thr Arg Gly Ala Val Leu Met Tyr Gln Gly
                  1525              1530              1535

Lys Arg Leu Glu Pro Ser Trp Ala Ser Val Lys Lys Asp Leu Ile Ser
                  1540              1545              1550

Tyr Gly Gly Gly Trp Arg Phe Gln Gly Ser Trp Asn Thr Gly Glu Glu
              1555              1560              1565

Val Gln Val Ile Ala Val Glu Pro Gly Lys Asn Pro Lys Asn Val Gln
         1570              1575              1580

Thr Ala Pro Gly Thr Phe Lys Thr Pro Glu Gly Glu Val Gly Ala Ile
1585              1590              1595              1600

Ala Leu Asp Phe Lys Pro Gly Thr Ser Gly Ser Pro Ile Val Asn Arg
                  1605              1610              1615

Glu Gly Lys Ile Val Gly Leu Tyr Gly Asn Gly Val Val Thr Thr Ser
                  1620              1625              1630

Gly Thr Tyr Val Ser Ala Ile Ala Gln Ala Lys Ala Ser Gln Glu Gly
              1635              1640              1645

Pro Leu Pro Glu Ile Glu Asp Glu Val Phe Arg Lys Arg Asn Leu Thr
              1650              1655              1660

Ile Met Asp Leu His Pro Gly Ser Gly Lys Thr Arg Arg Tyr Leu Pro
1665              1670              1675              1680

Ala Ile Val Arg Glu Ala Ile Arg Arg Asn Val Arg Thr Leu Ile Leu
                  1685              1690              1695

Ala Pro Thr Arg Val Val Ala Ser Glu Met Ala Glu Ala Leu Lys Gly
              1700              1705              1710

Met Pro Ile Arg Tyr Gln Thr Thr Ala Val Lys Ser Glu His Thr Gly
              1715              1720              1725

Lys Glu Ile Val Asp Leu Met Cys His Ala Thr Phe Thr Met Arg Leu
         1730              1735              1740

Leu Ser Pro Val Arg Val Pro Asn Tyr Asn Met Ile Ile Met Asp Glu
1745              1750              1755              1760

Ala His Phe Thr Asp Pro Ala Ser Ile Ala Arg Arg Gly Tyr Ile Ser
              1765              1770              1775

Thr Arg Val Gly Met Gly Glu Ala Ala Ala Ile Phe Met Thr Ala Thr
              1780              1785              1790

Pro Pro Gly Ser Val Glu Ala Phe Pro Gln Ser Asn Ala Val Ile Gln
         1795              1800              1805

Asp Glu Glu Arg Asp Ile Pro Glu Arg Ser Trp Asn Ser Gly Tyr Glu
         1810              1815              1820

Trp Ile Thr Asp Phe Pro Gly Lys Thr Val Trp Phe Val Pro Ser Ile
1825              1830              1835              1840

Lys Ser Gly Asn Asp Ile Ala Asn Cys Leu Arg Lys Asn Gly Lys Arg
              1845              1850              1855
```

-continued

Val Ile Gln Leu Ser Arg Lys Thr Phe Asp Thr Glu Tyr Gln Lys Thr
        1860                1865                1870

Lys Asn Asn Asp Trp Asp Tyr Val Val Thr Thr Asp Ile Ser Glu Met
1875                1880                1885

Gly Ala Asn Phe Arg Ala Asp Arg Val Ile Asp Pro Arg Arg Cys Leu
     1890                1895                1900

Lys Pro Val Ile Leu Lys Asp Gly Pro Glu Arg Val Ile Leu Ala Gly
1905                1910                1915                1920

Pro Met Pro Val Thr Val Ala Ser Ala Ala Gln Arg Arg Gly Arg Ile
          1925                1930                1935

Gly Arg Asn Gln Asn Lys Glu Gly Asp Gln Tyr Val Tyr Met Gly Gln
     1940                1945                1950

Pro Leu Asn Asn Asp Glu Asp His Ala His Trp Thr Glu Ala Lys Met
        1955                1960                1965

Leu Leu Asp Asn Ile Asn Thr Pro Glu Gly Ile Ile Pro Ala Leu Phe
     1970                1975                1980

Glu Pro Glu Arg Glu Lys Ser Ala Ala Ile Asp Gly Glu Tyr Arg Leu
1985                1990                1995                2000

Arg Gly Glu Ala Arg Lys Thr Phe Val Glu Leu Met Arg Arg Gly Asp
          2005                2010                2015

Leu Pro Val Trp Leu Ser Tyr Lys Val Ala Ser Glu Gly Phe Gln Tyr
        2020                2025                2030

Ser Asp Arg Arg Trp Cys Phe Asp Gly Glu Arg Asn Asn Gln Val Leu
        2035                2040                2045

Glu Glu Asn Met Asp Val Glu Met Trp Thr Lys Glu Gly Glu Arg Lys
     2050                2055                2060

Lys Leu Arg Pro Arg Trp Leu Asp Ala Arg Thr Tyr Ser Asp Pro Leu
2065                2070                2075                2080

Ala Leu Arg Glu Phe Lys Glu Phe Ala Ala Gly Arg Arg Ser Val Ser
          2085                2090                2095

Gly Asp Leu Ile Leu Glu Ile Gly Lys Leu Pro Gln His Leu Thr Gln
     2100                2105                2110

Arg Ala Gln Asn Ala Leu Asp Asn Leu Val Met Leu His Asn Ser Glu
        2115                2120                2125

Gln Gly Gly Arg Ala Tyr Arg His Ala Met Glu Glu Leu Pro Asp Thr
     2130                2135                2140

Ile Glu Thr Leu Met Leu Leu Ala Leu Ile Ala Val Leu Thr Gly Gly
2145                2150                2155                2160

Val Thr Leu Phe Phe Leu Ser Gly Lys Gly Leu Gly Lys Thr Ser Ile
          2165                2170                2175

Gly Leu Leu Cys Val Met Ala Ser Ser Val Leu Leu Trp Met Ala Ser
     2180                2185                2190

Val Glu Pro His Trp Ile Ala Ala Ser Ile Ile Leu Glu Phe Phe Leu
        2195                2200                2205

Met Val Leu Leu Ile Pro Glu Pro Asp Arg Gln Arg Thr Pro Gln Asp
2210                2215                2220

Asn Gln Leu Ala Tyr Val Val Ile Gly Leu Leu Phe Met Ile Leu Thr
2225                2230                2235                2240

Val Ala Ala Asn Glu Met Gly Leu Leu Glu Thr Thr Lys Lys Asp Leu
          2245                2250                2255

Gly Ile Gly His Val Ala Ala Glu Asn His His His Ala Thr Met Leu
     2260                2265                2270

Asp Val Asp Leu Arg Pro Ala Ser Ala Trp Thr Leu Tyr Ala Val Ala
     2275                2280                2285

-continued

```
Thr Thr Val Ile Thr Pro Met Met Arg His Thr Ile Glu Asn Thr Thr
    2290            2295            2300
Ala Asn Ile Ser Leu Thr Ala Ile Ala Asn Gln Ala Ala Ile Leu Met
2305            2310            2315            2320
Gly Leu Asp Lys Gly Trp Pro Ile Ser Lys Met Asp Ile Gly Val Pro
        2325            2330            2335
Leu Leu Ala Leu Gly Cys Tyr Ser Gln Val Asn Pro Leu Thr Leu Thr
        2340            2345            2350
Ala Ala Val Leu Met Leu Val Ala His Tyr Ala Ile Ile Gly Pro Gly
    2355            2360            2365
Leu Gln Ala Lys Ala Thr Arg Glu Ala Gln Lys Arg Thr Ala Ala Gly
    2370            2375            2380
Ile Met Lys Asn Pro Thr Val Asp Gly Ile Val Ala Ile Asp Leu Asp
2385            2390            2395            2400
Pro Val Val Tyr Asp Ala Lys Phe Glu Lys Gln Leu Gly Gln Ile Met
        2405            2410            2415
Leu Leu Ile Leu Cys Thr Ser Gln Ile Leu Leu Met Arg Thr Thr Trp
        2420            2425            2430
Ala Leu Cys Glu Ser Ile Thr Leu Ala Thr Gly Pro Leu Thr Thr Leu
    2435            2440            2445
Trp Glu Gly Ser Pro Gly Lys Phe Trp Asn Thr Thr Ile Ala Val Ser
    2450            2455            2460
Met Ala Asn Ile Phe Arg Gly Ser Tyr Leu Ala Gly Ala Gly Leu Ala
2465            2470            2475            2480
Phe Ser Leu Met Lys Ser Leu Gly Gly Gly Arg Arg Gly Thr Gly Ala
        2485            2490            2495
Lys Gly Lys His Trp Glu Arg Asn Gly Lys Asp Arg Leu Asn Gln Leu
        2500            2505            2510
Ser Lys Ser Glu Phe Asn Thr Tyr Lys Arg Ser Gly Ile Met Glu Val
    2515            2520            2525
Asp Arg Ser Glu Ala Lys Glu Gly Leu Lys Arg Gly Glu Thr Thr Lys
    2530            2535            2540
His Ala Val Ser Arg Gly Thr Ala Lys Leu Arg Trp Phe Val Glu Arg
2545            2550            2555            2560
Asn Leu Val Lys Pro Glu Gly Lys Val Ile Asp Leu Gly Cys Gly Arg
        2565            2570            2575
Gly Gly Trp Ser Tyr Tyr Cys Ala Gly Leu Lys Lys Val Thr Glu Val
        2580            2585            2590
Lys Gly Tyr Thr Lys Gly Gly Pro Gly His Glu Glu Pro Ile Pro Met
    2595            2600            2605
Ala Thr Tyr Gly Trp Asn Leu Val Lys Leu Tyr Ser Gly Lys Asp Val
    2610            2615            2620
Phe Phe Thr Pro Pro Glu Lys Cys Asp Thr Leu Leu Cys Asp Ile Gly
2625            2630            2635            2640
Glu Ser Ser Pro Asn Pro Thr Ile Glu Glu Gly Arg Thr Leu Arg Val
        2645            2650            2655
Leu Lys Met Val Glu Pro Trp Leu Arg Gly Asn Gln Phe Cys Ile Lys
        2660            2665            2670
Ile Leu Asn Pro Tyr Met Pro Ser Val Val Glu Thr Leu Glu Gln Met
    2675            2680            2685
Gln Arg Lys His Gly Gly Met Leu Val Arg Asn Pro Leu Ser Arg Asn
    2690            2695            2700
Ser Thr His Glu Met Tyr Trp Val Ser Cys Gly Thr Gly Asn Ile Val
```

-continued

```
            2705                2710                2715                2720
Ser Ala Val Asn Met Thr Ser Arg Met Leu Leu Asn Arg Phe Thr Met
                    2725                2730                2735
Ala His Arg Lys Pro Thr Tyr Glu Arg Asp Val Asp Leu Gly Ala Gly
                    2740                2745                2750
Thr Arg His Val Ala Val Glu Pro Glu Val Ala Asn Leu Asp Ile Ile
                    2755                2760                2765
Gly Gln Arg Ile Glu Asn Ile Lys His Glu His Lys Ser Thr Trp His
                    2770                2775                2780
Tyr Asp Glu Asp Asn Pro Tyr Lys Thr Trp Ala Tyr His Gly Ser Tyr
2785                2790                2795                2800
Glu Val Lys Pro Ser Gly Ser Ala Ser Ser Met Val Asn Gly Val Val
                    2805                2810                2815
Lys Leu Leu Thr Lys Pro Trp Asp Ala Ile Pro Met Val Thr Gln Ile
                    2820                2825                2830
Ala Met Thr Asp Thr Thr Pro Phe Gly Gln Gln Arg Val Phe Lys Glu
                    2835                2840                2845
Lys Val Asp Thr Arg Thr Pro Lys Ala Lys Arg Gly Thr Ala Gln Ile
                    2850                2855                2860
Met Glu Val Thr Ala Arg Trp Leu Trp Gly Phe Leu Ser Arg Asn Lys
2865                2870                2875                2880
Lys Pro Arg Ile Cys Thr Arg Glu Glu Phe Thr Arg Lys Val Arg Ser
                    2885                2890                2895
Asn Ala Ala Ile Gly Ala Val Phe Val Asp Glu Asn Gln Trp Asn Ser
                    2900                2905                2910
Ala Lys Glu Ala Val Glu Asp Glu Arg Phe Trp Asp Leu Val His Arg
                    2915                2920                2925
Glu Arg Glu Leu His Lys Gln Gly Lys Cys Ala Thr Cys Val Tyr Asn
                    2930                2935                2940
Met Met Gly Lys Arg Glu Lys Lys Leu Gly Glu Phe Gly Lys Ala Lys
2945                2950                2955                2960
Gly Ser Arg Ala Ile Trp Tyr Met Trp Leu Gly Ala Arg Phe Leu Glu
                    2965                2970                2975
Phe Glu Ala Leu Gly Phe Met Asn Glu Asp His Trp Phe Ser Arg Glu
                    2980                2985                2990
Asn Ser Leu Ser Gly Val Glu Gly Glu Gly Leu His Lys Leu Gly Tyr
                    2995                3000                3005
Ile Leu Arg Asp Ile Ser Lys Ile Pro Gly Gly Asn Met Tyr Ala Asp
                    3010                3015                3020
Asp Thr Ala Gly Trp Asp Thr Arg Ile Thr Glu Asp Asp Leu Gln Asn
3025                3030                3035                3040
Glu Ala Lys Ile Thr Asp Ile Met Glu Pro Glu His Ala Leu Leu Ala
                    3045                3050                3055
Thr Ser Ile Phe Lys Leu Thr Tyr Gln Asn Lys Val Val Arg Val Gln
                    3060                3065                3070
Arg Pro Ala Lys Asn Gly Thr Val Met Asp Val Ile Ser Arg Arg Asp
                    3075                3080                3085
Gln Arg Gly Ser Gly Gln Val Gly Thr Tyr Gly Leu Asn Thr Phe Thr
                    3090                3095                3100
Asn Met Glu Ala Gln Leu Ile Arg Gln Met Glu Ser Glu Gly Ile Phe
3105                3110                3115                3120
Ser Pro Ser Glu Leu Glu Thr Pro Asn Leu Ala Glu Arg Val Leu Asp
                    3125                3130                3135
```

```
Trp Leu Glu Lys Tyr Gly Val Glu Arg Leu Lys Arg Met Ala Ile Ser
        3140                3145                3150

Gly Asp Asp Cys Val Val Lys Pro Ile Asp Asp Arg Phe Ala Thr Ala
        3155                3160                3165

Leu Thr Ala Leu Asn Asp Met Gly Lys Val Arg Lys Asp Ile Pro Gln
    3170                3175                3180

Trp Glu Pro Ser Lys Gly Trp Asn Asp Trp Gln Gln Val Pro Phe Cys
3185                3190                3195                3200

Ser His His Phe His Gln Leu Ile Met Lys Asp Gly Arg Glu Ile Val
            3205                3210                3215

Val Pro Cys Arg Asn Gln Asp Glu Leu Val Gly Arg Ala Arg Val Ser
        3220                3225                3230

Gln Gly Ala Gly Trp Ser Leu Arg Glu Thr Ala Cys Leu Gly Lys Ser
        3235                3240                3245

Tyr Ala Gln Met Trp Gln Leu Met Tyr Phe His Arg Arg Asp Leu Arg
        3250                3255                3260

Leu Ala Ala Asn Ala Ile Cys Ser Ala Val Pro Val Asp Trp Val Pro
3265                3270                3275                3280

Thr Ser Arg Thr Thr Trp Ser Ile His Ala His His Gln Trp Met Thr
            3285                3290                3295

Thr Glu Asp Met Leu Ser Val Trp Asn Arg Val Trp Ile Glu Glu Asn
        3300                3305                3310

Pro Trp Met Glu Asp Lys Thr His Val Ser Ser Trp Glu Asp Val Pro
        3315                3320                3325

Tyr Leu Gly Lys Arg Glu Asp Gln Trp Cys Gly Ser Leu Ile Gly Leu
        3330                3335                3340

Thr Ala Arg Ala Thr Trp Ala Thr Asn Ile Gln Val Ala Ile Asn Gln
3345                3350                3355                3360

Val Arg Arg Leu Ile Gly Asn Glu Asn Tyr Leu Asp Tyr Met Thr Ser
        3365                3370                3375

Met Lys Arg Phe Lys Asn Glu Ser Asp Pro Lys Gly His Ser Gly Glu
        3380                3385                3390

Ser Thr His Leu
        3395

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCATGAATTC CCATGCGATG CGTGGGA                                            27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CACATCTCGA GTCCGCTTGA ACCATGA                                            27
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGGTTCCCGG GGACTCGGGA TGTGTA      26

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ACTAAGCTTG ATCATGCAGA GACCATTGA      29

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AATCAGAATT CTCTGCAGGG TCAGGGGAA      29

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATAACAAAGC TTATCTTTGT TTCTTTTTCT      30

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GAAAGGATCC TCTGGAGTGT TATGGGACAC A      31

(2) INFORMATION FOR SEQ ID NO:10:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ACCCAAGCTT CATCTTCTTC CTGCTGC                                    27

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGGAGGTCGA CGAGGTACGG GAGCC                                      25

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAATGATATC TAGGTTGGCT                                            20

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCGTGAATCC TGGGTGTC                                              18

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGGAATTCCA GTGGTGTGGA TC                                         22

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GTAAAACGAC GGCCAGT                                                    17

(2) INFORMATION FOR SEQ ID NO:16:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:16:

Met Met Asn Gln Arg Lys Lys
1               5

(2) INFORMATION FOR SEQ ID NO:17:

(i) SEQUENCE CHARACTERISTICS:
             (A) LENGTH: 4 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:17:

Ala Phe Xaa Leu
1

(2) INFORMATION FOR SEQ ID NO:18:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:18:

Arg Xaa Lys Arg Ser Val
1               5

(2) INFORMATION FOR SEQ ID NO:19:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:19:

Xaa Met Arg Cys Xaa Gly
1               5

(2) INFORMATION FOR SEQ ID NO:20:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:20:

Val Gln Ala Asp Xaa Gly Cys Val
1               5

(2) INFORMATION FOR SEQ ID NO:21:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Val Xaa Ala Gly Xaa Gly
1               5

(2) INFORMATION FOR SEQ ID NO:22:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Xaa Ser Trp Pro Leu Asn
1               5

(2) INFORMATION FOR SEQ ID NO:23:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Lys Xaa Gln Arg Xaa Gly
1               5

(2) INFORMATION FOR SEQ ID NO:24:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Gly Arg Xaa Ser
1

(2) INFORMATION FOR SEQ ID NO:25:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide -continued (xi) SEQUENCE DESCRIPTION: SEQ ID NO:25:

```
Val Xaa Ala Asn Glu
1               5
```

CDNA SEQUENCE OF DENGUE VIRUS SEROTYPE 1 (SINGAPORE STRAIN)

The present invention relates to Dengue Virus Type 1. Dengue virus infection may lead to dengue fever (DF) or its more severe dengue haemorrhagic fever (DHF) and dengue shock syndrome (DSS). DHF is an important virus disease of global significance, especially in Southeast Asia. There are four serotypes of Dengue virus (DEN1, DEN2, DEN3 and DEN4) belonging to the family Flaviviradae.

The complete genomic sequence of DEN2 (Jamaica) has been published by Deubel et al; Virology 165, 234–244 (1988). The complete genomic sequence of DEN3 (HS87) has been published by Osatomi and Sumiyoshi; Virology 176, 643–647 (1990). The complete genomic sequence of DEN4 has been published by Zhao et al; Virology 155, 77–88. To date, only a partial sequence of any variant of DEN1, DEN1 (Nauru Island), has been determined; Mason et al, Virology 161, 262–267 (1987).

We have now identified a previously unknown strain of DEN1 and established its complete nucleotide sequence. The new strain, DEN1-S275/90, was deposited at the European Collection of Animal Cell Cultures (ECACC) Porton Down, GB under Budapest Treaty conditions on (Apr. 21, 1992) and given accession number V92042111. DEN1-S275/90 differs significantly from DEN2, DEN3 and DEN4 in terms of sequence homology. There are also a number of significant differences between DEN1-S275/90 and DEN1 (Nauru Island).

The present invention thus provides DEN1-S275/90 (ECACC V92042111). The invention further provides DEN1-S275/90 (ECACC V92042111) for use as a diagnostic reagent. The invention also provides DEN1-S275/90 in inactivated form for use as a diagnostic reagent or a vaccine.

The invention also provides the nucleic acid sequence of Seq. ID No. 1 and DNA sequences substantially corresponding to SEQ ID No. 1, e.g. degenerate variants thereof having one or more nucleotide changes but nevertheless capable of being translated to give the same protein sequence. The invention further provides fragments of such DNA polynucleotides, in particular the fragments encoding the C, C', PreM, M, E, NS1, NS2A, NS2B, NS3, NS4A, NS4B and NS5 genes of the genome of the virus. The start and end points of these preferred fragments in the nucleic acid sequence of Seq I.D. No. 1 are shown below in Table 1. Table 1 also shows the start and end points of the proteins encoded by these genes, using the numbering of Seq. ID Nos. 1 and 2.

TABLE 1

Start and end points of the nucleic acid (n) numbers encoding the genes of S275/90. The table also shows the start and end points of the corresponding proteins (p) within the polyprotein encoded by S275/90.

| Gene | Start(n) | End(n) | Start(p) | End(p) |
|---|---|---|---|---|
| C | 81 | 422 | 1 | 114 |
| C' | 123 | 422 | 15 | 114 |
| PreM | 423 | 695 | 115 | 205 |
| M | 696 | 920 | 206 | 280 |
| E | 921 | 2402 | 281 | 774 |
| NS1 | 2403 | 3464 | 775 | 1128 |
| NS2A | 3465 | 4112 | 1129 | 1344 |
| NS2B | 4113 | 4499 | 1345 | 1474 |
| NS3 | 4500 | 6359 | 1475 | 2093 |
| NS4A | 6360 | 6809 | 2094 | 2242 |
| NS4B | 6810 | 7556 | 2243 | 2492 |
| NS5 | 7557 | 10268 | 2493 | 3396 |

The nucleic acid sequences of the invention may be used as probes in an assay to determine the presence or absence of DEN1-S275/90, or they may be incorporated into a vector, eg. an expression vector.

Nucleic acid fragments according to the invention may be made by known methods of chemical synthesis or cloned from the virus itself using known recombinant techniques. Fragments according to the invention may also be produced by replication of DNA or RNA, by transcription from DNA to form RNA fragments or reverse transcription from RNA fragments to form DNA fragments. Such transcription may be in a cell free system or may be effected in cells for instance by cloning. Cell free systems include an appropriate replicase, transcriptase or reverse transcriptase, suitable nucleotide precursors and a nucleic acid template or appropriate sequence, together with buffers and any necessary or desirable cofactors.

The present invention also provides a polyprotein as set forth in Seq. ID No. 1 and Seq. ID No. 2 and fragments thereof, eg. the C, C', PreM, M, E, NS1, NS2A, NS2B, NS3, NS4A, NS4B and NS5 proteins as identified above in Table 1. The invention thus provides a polypeptide having an amino acid sequence substantially corresponding to the sequence shown in SEQ ID No. 2 or a fragment thereof. Fusion proteins which incorporate these peptides are also provided.

The polyprotein and proteins according to the invention may be produced by synthetic peptide chemistry or by expressing vectors carrying DNA encoding the proteins in a suitable cell in order to produce expression of the DNA, followed by recovery of the expressed protein. Methods of expressing and recovering recombinant proteins, including fusion proteins, are well known in the art.

For example, for expression of a polypeptide of the invention, an expression vector may be constructed. An expression vector is prepared which comprises a DNA sequence encoding a polypeptide of the invention and which is capable of expressing the polypeptide when provided with a suitable host, eucaryotic or procaryotic. Appropriate transcriptional and translational control elements are provided, including a promoter for the DNA sequence, a transcriptional termination site, and translational start and stop codons. The DNA sequence is provided in the correct frame such as to enable expression of the polypeptide to occur in a host compatible with the vector. The expression vector may be selected to be suitable to express the nucleic acid sequences of the invention in, for example, a bacterial e.g. E. coli, yeast, insect or mammalian cell. A baculovirus expression system may be used. The nucleic acid may be expressed in order that a protein or peptide encoded by the fragment alone is produced or alternatively it may be expressed to provide a fusion protein in which DEN1-S275/90 or a protein thereof, e.g. E, NS1, NS2, NS3 or NS5 as identified in Table 1 above is fused to a second amino acid sequence, e.g. a C-terminal sequence derived from glutathione S-transferase or maltose binding protein or a C-terminal or N-terminal signal sequence. Such a sequence may for example cause the fusion protein to be exported from the cell. The expression vector is then provided with an appropriate host. Cells harbouring the vector are grown so as to enable expression to occur. The vector may be a plasmid or a viral vector.

Recovery and where desirable, further purification of the protein produced by an expression vector in a host cell may be by means known in the art. Such means are designed to separate the protein of the invention from the other proteins of the host cell. Suitable means include chromatographic separation of the recovered protein.

The polyprotein and peptides of the invention may be used as immunogens for a vaccine against DEN1-S275/90 and other DEN1 viruses. Suitably, the proteins and peptides of the invention will be combined with a pharmaceutically acceptable carrier or diluent in order to prepare a sterile vaccine composition. The vaccine composition may then be used in a method of immunizing a human against DEN1 infections.

Advantageously, a vaccine composition against DEN1 may comprise a mixture of two or more peptides. For example, it may comprise one non-structural (NS) peptide, eg. NS1 or NS3, together with a capsid (C), M or E peptide. A mixture of two or more NS peptides could also be used.

The proteins and peptides of the invention may also be used as antigens in an immunoassay to detect the presence or absence of DEN1, and especially DEN1-S275/90. The proteins and peptides are optionally labelled with a detectable label, eg a radioisotope, biotin or a fluorophore. The immunoassay may be conducted by bringing a known quantity of labelled protein (antigen) into contact with a sample suspected of containing antibody against DEN1 and detecting the presence or absence of antibody-antigen complex containing the labelled antigen.

The invention also provides antibodies against the above-mentioned proteins and peptides of the invention. The antibodies may be monoclonal or polyconal. Monoclonal antibodies may be produced by hybridoma techniques known in the art or by recombinant means to provide hybrid antibodies such as humanized antibodies.

The antibodies of the invention may be used in a method of treatment, eg passive immunisation, of DEN1 infections. The antibodies may also be used in a method of diagnosis, eg by immunoassay, to detect the presence or absence of DEN1 in a sample. The antibodies may be labelled as described above for the proteins and peptides of the invention. They may also be labelled with a toxin or isotope selected to kill virus-infected cells. Antibodies against NS1 are particularly favoured since NS1 is expressed on the surface of Dengue virus-infected cells.

The antibodies of the invention may also be used in a method to detect the presence or absence of DEN1 protein in a sample. The method may comprise bringing the antibody into contact with a sample suspected to contain DEN1 proteins (antigens) and detecting the amount of antibody-antigen complex formed. Immunoassays according to the invention may be, for example, competitive (eg radioimmune assays—RIA) or non-competitive (eg enzyme linked immunosorbent assays—ELISA).

The following Examples illustrate the invention. In the accompanying drawings:

FIG. 1 is a diagrammatic representation of the cDNA of Dengue virus Type 1 (Singapore strain S275/90) and fragments of said DNA in expression vectors;

FIG. 2 shows gel results confirming serologic responses in mice after immunisations with fusion proteins prepared as in Examples 2–5 with or without complete Freund's adjuvant (CFA).

Gel Lanes: Lane 1: M, Lane 2: anti E, Lane 3: anti-E+ CFA, Lane 4: anti-NS1, Lane 5: anti-NS2, Lane 6: anti-NS2+ CFA, Lane 7: anti-NS3, Lane 8: anti-NS3+ CFA, Lane 9: anti-NS5, Lane 10: anti-NS5+ CFA, Lane 11: positive rabbit sera, Lane 12: negative rabbit sera, Lane 13: M;

FIG. 3 shows gel results confirming serologic response in rabbits after immunisations with fusion proteins prepared as in Examples 2 to 5. (−), serum before immunisation; (+) serum after immunisation.

Gel Lanes: Lane 1: (−), Lane 2: (+) anti-E, Lane 3: (−), Lane 4: (+) anti-NS1, Lane 5: (−), Lane 6: (+) anti-NS2, Lane 7: (−), Lane 8: (+) anti-NS3, Lane 9: (−), Lane 10: (+) anti-NS5, Lane 11: positive Dengue, Lane 12: patient sera;

FIG. 4 shows fluorescence microscopy of C6/36 cells infected with Dengue Type 1 DI-275 and probed with antibodies against recombinant fusion proteins. A, control antiserum; B, anti-E; C, anti-NS1; D, anti-NS2; E, anti-NS3; F anti-NS5.

EXAMPLE 1

DEN1 virus, strain S275/90, was isolated in 1990 from the serum of a DHF patient in Singapore by 3 passages in AP61 (*Aedes psuedoscutellaris*) cells followed by 3 passages in C6/36 (*Aedes albopictus*) cells, and identified by immunofluorescence using type-specific monoclonal antibodies. After a further 8 to 13 passages in C6/36 cells, the virus-infected culture fluid was partially purified by precipitation with polyethylene glycol and ultracentrifugation on a 30% sucrose cushion (6). The viral RNA was extracted from the purified virus by treatment with phenol in the presence of sodium dodecyl sulphate. Following cDNA synthesis (cDNA Synthesis System Plus, Amersham) using random primers, the assorted cDNAs were cloned into EcoRI sites of pUC18 vector via EcoRI adaptors (Promega). The *Esherichia coli* transformants containing Dengue-specific sequences were screened by colony hybridisation with $^{32}P$-labelled cDNA probes prepared by reverse transcription of strain S275/90 RNA. The cloning procedure yielded overlapping cDNA clones containing inserts ranging in size from 0.5 kb to 2.7 kb. The ends of these primary clones and their subclones obtained by nested deletional analysis (Erase-a-Base System, Promega) were subjected to double-strand sequencing (Sequenase Version 2.0, United States Biochemical). The sequence data generated covers about 90% of the genomic sequence of S275/90.

Potential secondary structures have been postulated for the 5' and 3' ends of flaviviruses (4, 7, 8), posing a problem in obtaining clones with intact ends. A different stragegy for sequencing the 5' and 3' noncoding regions was used to increase the chances of obtaining clones which contain these sequences as well as the terminal end sequences of the genome. cDNAs of strain S275/90 were obtained by random priming and oligo(dT) priming (after poly(A) tailing of the virus RNA]; these were amplified by polymerase chain reaction (PCR) in the presence of specific primers, 796 and 10090/B, respectively. The cDNAs of interest were then religated into pUC18 vector. The nucleotide sequences of the primers are as follows: primer 796, 5' CCG TGA ATC CTG GGT GTC 3' (SEQ ID NO: 13); primer 10090/B, 5' GGG AAT TCC AGT GGT GTG GATC 3' (SEQ ID NO:14) with a BamHI site at its 5' end. The sequences of the primers were selected from that of the initial clones of strain S275/90. To obtain the sequences at the 5' noncoding region, random cDNA clones were first generated as described above, followed by ligation to EcoRI adaptors before insertion into the EcoRI sites of the pUC18 vector. These ligated products of assorted cDNA inserts were flanked by the reverse and forward sequencing primers of M13 in the pUC18 vector. The forward sequencing primer was thus used as one of the primers for PCR. The ligated cDNA clones were used as templates for PCR in the presence of primer 796 (which binds to the plus strand of the template at nucleotide position 808 to 825 of strain S275/90) and the commercial M13 single-strand primer (5'GTA AAA CGA CGG CCAGT 3' (SEQ ID NO: 15), Pharmacia). The amplified cDNAs thus contained the polylinker from the pUC18 vector at one end and an XbaI site (at nucleotide position 728) at the other end. For the 3' noncoding region, an additional step was included before cDNA synthesis. After extraction, the purified Dengue viral RNA was tailed by poly A polymerase (Bethesda Research Laboratories) with ATP. This was followed by cDNA synthesis using oligo(dT) as primer for the first strand cDNA synthesis. The same procedures of EcoRI adaptors ligation and insertion into EcoRI sites of the pUC18 vector were repeated. The ligated products were again subjected to PCR amplification using the primer 10090/B (which binds to the minus strand of the template at nucleotide positions 10,086 to 10,099 of strain S275/90) and the commercial M13 single-strand primer.

All samples were amplified by 30 cycles of PCR with melting, annealing and polymerisation conditions of 1 minute at 94° C., 2 minutes at 55° C. and 3 minutes at 72° C., respectively. The amplified DNA was purified by electroelution in agarose gel followed by appropriate restriction enzyme digestions. The PCR amplified cDNAs at the 5' noncoding region were double digested with XbaI and EcoRI, while those at the 3' noncoding region were digested with BamHI and EcoIR before cloning into the appropriate sites of the pUC18 vector. The clones were screened and subjected to double-strand sequencing as described above.

The sequence data obtained from the overlapping cDNA clones was ordered by homology alignment with the published sequences of the four Dengue serotypes DEN1, DEN2, DEN3 and DEN4 using the computer program of Wilbur and Lipman (9). Seq ID No. 1 shows the complete nucleotide sequence of strain S275/90, which is 10,718 nucleotides in length, and its deduced amino acid sequence. The reading frame begins with the first AUG start codon, corresponding to nucleotides 81 to 83, and contains an open reading frame of 10,188 nucleotides encoding a polyprotein of 3396 amino acids; there are 80 nucleotides in the 5' noncoding region and 450 nucleotides in the 3' noncoding region. The sequence in the 5' noncoding region preceding the first AUG codon of the open reading frame appears to be conserved for all Dengue virus types (1–4). The length of the 3' noncoding region of strain S275/90 is longer than that of DEN2 (412 nucleotides), DEN3 (433 nucleotides) and DEN4 (384 nucleotides).

The nucleotide composition of strain S275/90 is 31.9% A, 25.9% G, 21.5% T and 20.7% C. As reported for the other flaviviruses, the same purine-rich composition was observed, and there is an absence of poly(A) tract at the 3' end.

The individual protein coding segments are based on comparison with protein sequence data for all the proteins determined from the four Dengue serotypes. These cleavage sites may reveal the involvement of viral or cellular proteases involved in protein processing. The C, preM, M, E, NS1, NS2A, NS2B, NS3, NS4A, NS4B and NS5 proteins are cleaved at the sites M/MNQRKK, A/FXL, RXKR/SV, X/MRCXG, VQA/DXGCV, VXA/GXG, X/SWPLN, KXQR/XG, GRX/S, VXA/NE (SEQ ID NO:s 16–25, respectively) and R/G, respectively, where X refers to any residue. The cleavage sites of NS2A, NS3 and NS4B conform to the reported consensus sequences (4, 5), which were originally established by Rice et al (10).

The nucleotide sequences of the structural and nonstructural regions (5' noncoding end to NS1, about 2400 nucleotides in length) of Nauru Island strain of DEN1 (isolated in 1974) and strain S275/90 were compared. Nucleotide variation shows that transitions are about 85.0% [transitions/(transitions+transversions)×100%] in the structural region and 92.1% in the NS1 region; 15% of these base changes are transversions in the structural region and 7.9% in the NS1 region. The overall 236 nucleotide differences have given rise to 27 amino acid substitutions. As shown in Table 2, the nucleotide homology is 93.1% and when translated, the amino acid homology is 97.6%. Although both strains were isolated from different geographic regions with an interval of 16 years, a higher homology was still observed between the two strains. It can also be seen in Table 2 that strain S275/90 shows a higher homology with DEN3 then with DEN2 and DEN4. The nucleotide divergence of each gene is less than the translated amino acid divergence. The greatest nucleotide and amino acid changes, and hence the greatest evolution, lie in the nonstructural gene NS2A in all the four Dengue serotypes. A high homology is found in NS3 and NS5, which contain conserved sequences.

Chu et al (11) compared three topotypes of DEN1 strains (Thailand, Philippines and Caribbean) genetically at the envelope region. They found nucleotide changes to be less than 5% but translational differences of 2% at the amino acid level. Our strain S275/90 shows nucleotide changes of 7.7% and amino acid changes of 2.6% in the envelope region. Rico-Hesse (6) compared nucleotide sequences within a chosen E/NS1 region to estimate evolutionary relationships among 40 DEN1 strains of different geographic range and time period.

TABLE 2

HOMOLOGY (%) COMPARISON OF ALIGNED NUCLEOTIDE SEQUENCES OF THE FOUR DENGUE SEROTYPES WITH STRAIN S275/90 (AMINO ACID ALIGNMENT WITHIN BRACKETS).

| S275/90 | DEN1 | DEN2 | DEN3 | DEN4 |
|---|---|---|---|---|
| Full length | 93.1 (97.6) | 67.1 (70.9) | 70.4 (75.5) | 65.1 (67.6) |
| 5' non-coding | 100 | 81.7 | 93.8 | 87.7 |
| C | 97.4 (98.2) | 70.5 (67.5) | 80.5 (80.7) | 68.1 (67.9) |
| PrM | 91.6 (95.6) | 71.1 (75.8) | 75.8 (78.0) | 68.0 (68.1) |
| M | 93.3 (98.7) | 64.0 (70.7) | 70.3 (78.7) | 60.7 (60.3) |
| E | 92.3 (97.4) | 65.4 (67.7) | 69.0 (76.4) | 64.8 (61.8) |
| NS1 | 92.6 (98.0) | 70.1 (73.6) | 74.5 (78.7) | 70.1 (68.8) |
| NS2A | — | 55.1 (39.0) | 57.0 (46.8) | 51.7 (37.9) |
| NS2B | — | 66.0 (60.8) | 69.4 (69.2) | 63.1 (60.8) |
| NS3 | — | 72.0 (79.3) | 74.0 (84.5) | 69.9 (75.4) |
| NS4A | — | 63.0 (61.4) | 69.6 (68.7) | 62.8 (58.7) |
| NS4B | — | 69.7 (76.7) | 74.9 (82.3) | 71.1 (75.9) |
| NS5 | — | 71.7 (78.7) | 73.8 (81.0) | 69.9 (72.9) |
| 3' non-coding | — | 83.8 | 87.4 | 79.5 |

REFERENCES

1. WESTAWAY, E. G., BRINTON, M. A., GAIDAMOVICH, S. Ya, HORZINEK, M. C., IGARASHI, A., KAARIAINEN, L., LVOV, D. K., PORTERFIELD, J. S., RUSSEL, P. K., and TRENT, D. W., Intervirology 24, 183–192 (1985).

2. ROSEN, L., Supplement to S. Afr. J. Med. 11, 40–42 (1986).

3. HALSTEAD, S., Science 239, 476–481 (1988).
4. DEUBEL, V., KINNEY, R. M., and TRENT, D. W., Virology 165, 234–244 (1988).
5. OSATOMI, K. and SUMIYOSHI, H., Virology 176, 643–647 (1990).
6. RICO-HESSE, R., PALLANSCH, M. A., NOTTAY, B. K., AND KEW, O. M., Virology 174, 479–493 (1990)
7. BRINTON, M. A., and DISPOTO, J. H., Virology 162, 290–299 (1988).
8. IRIE, K., MOHAN, P. M., SASAGURI, Y., PUTNAK, R. and PADMANABHAN, R., Gene 75, 197–211 (1989).
9. WILBUR, W. J., and LIPMAN, D. J., Proc. Natl. Acad. Sci. USA 80, 726–730 (1983).
10. RICE, C. M., LENCHES, E. M., EDDY, S. R., SHIN, S. J., SHEETS, R. L., and STRAUSS, J. H., Science 229, 726–733 (1985).
11. CHU, M. C., O'ROURKE, E. J. and TRENT, D. W., J. Gen. Virol. 70, 1701–1712 (1989).

EXAMPLE 2
Construction of Expression Plasmids

Standard recombinant DNA techniques were used for construction of the expression plasmids described below and summarised in FIG. 1 (Sambrook et al., Molecular Cloning: a laboratory manual. Cold Spring Harbor Laboratory Press, N.Y.).

For construction of plasmids, the cDNA regions for E, NS1, NS2, NS3 and NS5 of clone DI-275, a DEN1 cDNA clone derived from DEN1 virus Singapore Strain S275/90 as in Example 1, were amplified by the polymerase chain reaction (PCR) and digested with restriction enzymes. The restriction enzyme sites were built into the oligonucleotide primers used in the PCR as set out in Table 3 and Seq ID Nos. 3–12.

Fragments of E, NS3 and NS5 cDNA digested with restriction enzymes were ligated to the pGEX-KG vector (Guan and Dixon, Anal. Biochem. 192, 262–267, 1991). Fragments of NS1 and NS2 cDNA were ligated to pMAL-c and pMAL-cRI vectors (New England Biolabs), respectively (Ford et al., Prot. Exp. Pur. 2, 96–107, 1991; Maina et al., Gene 74, 365–373, 1988; di Guan et al., Gene, 67, 21–30, 1991). The construction of NS5 cDNA was done in two stages. The 5'-region, the cDNA fragment from nucleotide 7544–8365 of NS5, was made by PCR, digested with SalI and ClaI; and the 3'-region, the fragment from nucleotide 8275 (ClaI) to the 3'-end of NS5, was isolated directly from the cDNA of clone DI-275 (D-275 cDNA) by ClaI and SacI double digestion. The two parts of NS5 were ligated together, then ligated into the pGEX-KG vector. Recombinant plasmids were transformed into E. coli DH5α or c600 HF1 strains. All plasmids encoded Dengue virus proteins fused to the C-terminus of glutathione S-transferase or Maltose Binding Protein (MBP).

EXAMPLE 3
Purification of E, Ns3 And Ns5 Proteins from Recombinant E. Coli

E. coli, harbouring E, NS3 and NS5 genes (separately) were grown in LB medium $A_{600}$ of 0.5 at 37° C., then induced with IPTG at 0.2 mM for 2 h at 30° C. The bacteria were harvested and resuspended on ice in MTPBS buffer (0.15 M NaCl, 0.016 M $Na_2HPO_4$, 0.005 M $NaH_2PO_4$) with 0.1 mg/ml lysozyme, 1% triton X-100, 0.5 µg/ml aprotinin, 0.05 µg/ml Leupeptin, 0.25 µg/ml pepstatin, 5 mM DTT and 0.175 µg/ml PMSF, and kept on ice for 10 min. The cells were sonicated at maximum power for 3×1 min while chilled. The lysate was centrifuged at 12,000× g. The supernatant was added to 1 ml Glutathione-Sepharose 4B beads (Pharmacia), and incubated at 4° C. on a rotator for 1 h to absorb the fusion proteins. Then the beads were centrifuged and washed with PBS buffer (by centrifugation) at least 6 times, or until the wash solution read zero at $A_{280}$ in a spectrophotometer. The beads were resuspended in thrombin cleavage buffer, and the Dengue virus proteins were cleaved off the beads with thrombin at 4° C. for 1 hr. The supernatant, containing Dengue virus proteins, was recovered by centrifugation, and the proteins were stored at −80° C.

EXAMPLE 4
Solubilisation and Purification of a Fusion Protein of NS1 from Inclusion Bodies E. coli containing the NS1 fusion protein was grown as above, except the tac promoters were induced with 0.3 mM IPTG for 16 h. The bacteria were harvested, 1 gram wet weight of E. coli was resuspended in 5 ml lysis buffer with lysozyme at 1.6 mg/ml and was sonicated for 2×15 sec. After centrifugation at 1000× g the supernatant was again centrifuged (25,000× g). The pellet was resuspended in 2 ml $H_2O$, adding a final concentration of 0.5% Triton X-100, 10 mM EDTA, and 100 mM NaCl, then centrifuged at 20,000× g twice. The pellet was washed with 1 ml 2 M urea twice and dissolved in 8 M urea in 0.1 M Tris-HCl pH 8.8, 0.14 M 2-mercaptoethanol. The urea concentration was reduced to 1 M by adding $H_2O$, and amylose resin (New England Biolabs) was added to adsorb the solubilised fusion protein at 22° C. for 1 h. The amylose resin was washed with buffer (New England Biolabs) five times until the $A_{280}$ of the clarified supernatant was near zero. A final concentration of 50 mM maltose was then added to elute the fusion protein, which was recovered by removing the beads by centrifugation.

EXAMPLE 5
Purification of a Soluble Fusion Protein of NS2

After growth of E. Coli transformed with pMAL-cRI/NS2-1, lysis and sonication as in Example 3 above, the clarified extract containing the soluble NS2 fusion protein was adsorbed onto amylose resin, followed by washing and elution of the NS2 fusion protein as in Example 4 above.

EXAMPLE 6
Immunisation of Rabbits and Mice

The soluble fusion proteins of E, NS2, NS3 and NS5 purified from recombinant E. coli, as in Examples 3 and 5 above, and inclusion bodies containing the NS1 fusion protein which had been purified up to the 2M urea wash stage as in Example 4, were placed directly in SDS loading buffer for preparative SDS-PAGE in 10% SDS-polyacrylamide gels. The proteins were visualised by staining with 0.05% Coomassie Blue for 10 min. The gel segments were cut and homogenized in sterile PBS, mixed with Freund's adjuvant and injected directly into white rabbits intramuscularly and subcutaneously on the first, sixth and twenty first days with about 200–500 µg of fusion protein per injected dose. The rabbits were bled 14 days after the last booster dose. For immunisation of mice, 12-day old female Swiss mice were immunised with the soluble proteins of E, NS1, NS2, NS3 and NS5 fusion proteins with or without Freund's adjuvant. The injections were intraperitoneal or subcutaneous on the first, fourth, and fourteenth day, using about 20 µg fusion protein per dose. The mice were bled 14 days after the last dose. The sera of rabbits and mice were used for IFA and immunoprecipitation assays.

EXAMPLE 7

Radioimmunoprecipitations

Radioimmunoprecipitations were done with rabbit and mouse antibodies against the structural and non-structural Dengue virus recombinant fusion proteins of D-275. At 36–40 h post-infection of C6/36 cells with Dengue virus S275/90 strain, cell culture medium was replaced with methionine-free medium containing 3 μg/ml actinomycin D for 3 h, followed by the addition of fresh medium with [$^{35}$S] methionine at 20 μCi/ml and 3 μg/ml actinomycin D for a further 3 h. The cells were washed with cold PBS, dissolved in RIPA buffer [100 mM Tris-HCl pH7.5, 150 mM NaCl, 10 mM EDTA, 0.1% SDS, 0.1% NP 40, 1% sodium dexoycholate, 100 μg/ml PMSF] on ice for 1 h, then clarified at 1000× g for 10 min. The lysates were precleared with normal serum and protein A Sepharose. For immunoprecipitation, rabbit and mouse sera that had been preabsorbed with normal, uninfected C6/36 cell extract fixed by cold acetone were incubated with labeled antigen overnight at 4° C. The virus protein-antibody complexes were precipitated with protein A-Sepharose and were washed with immunoprecipitation buffer [10 mM Tris-HCl, pH7.4, 0.05% aprotinin, 1% NP40, 2 mM EDTA, 0.15 M NaCl], 6 times then 2× SDS-PAGE buffer was added, boiled for 2 min, and the supernatant was loaded on a 12% SDS-polyacrylamide gel. After fixing enhancing and drying, the gel was exposed to X-ray film. The results confirmed that antibodies to recombinant E, NS1, NS2, NS3 and NS5 had been generated in mice (FIG. 2) and in rabbits (FIG. 3). These antibodies reacted with the native E, NS1, NS2, NS3 and NS5 proteins synthesised in infected C6/36 cells.

EXAMPLE 8

Indirect Immunofluorescence Assay

Figure 4D:
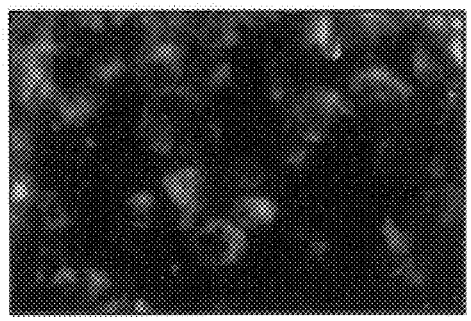
Figure 4B:
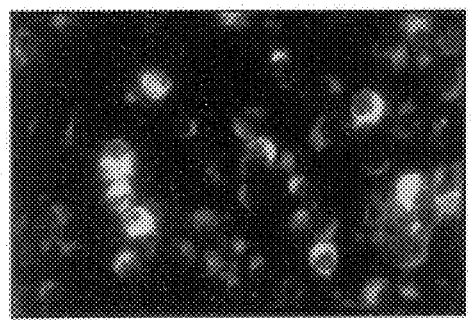
Figure 4E:
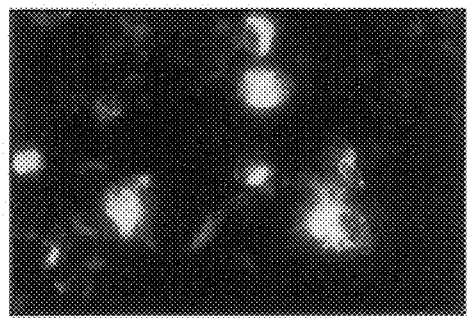
Figure 4C:
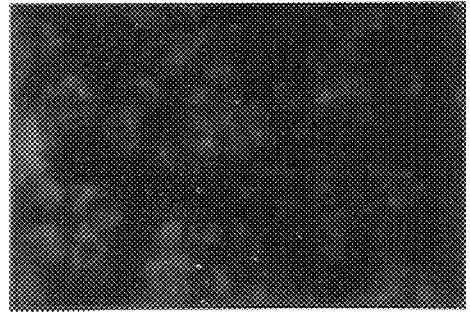
Figure 4F:
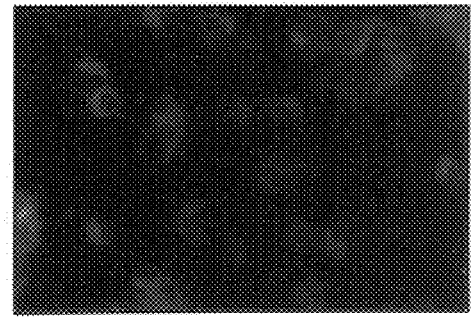

The C6/36 cells infected with Dengue virus S275/90 for 2 days were fixed on glass plates with cold acetone for immunofluorescence. 2-fold dilutions of the sera of rabbits or mice were incubated with the fixed cells for 1 h at 37° C., then washed with PBS. Secondary antibodies were linked to fluorescein and incubated for 1 h, followed by washing with PBS for observation using fluorescence microscopy. FIG. 4 shows the antisera to E, NS1, NS2, NS3 and NS5 reacted specifically with the Dengue virus S275/90 infected cells, but control antiserum did no react. Quantitation of the result (as set out in Table 4) showed that an immune response to all recombinant Dengue virus proteins (E, NS1, NS2, NS3 and NS5) occurred in both mice and rabbits.

TABLE 3

Oligonucleotides used to prepare cDNA fragments corresponding to Dengue virus proteins (by PCR)

1. pGEX-KG/EX-20

DIF920E  EcoRI        E
    5'CCA TGA ATT CCC ATG CGA TGC GTG GGA
    (SEQ ID NO:3)

DIF2400X  XhoI        E
    5'CAC ATC TCG AGT CCG CTT GAA CCA TGA
    (SEQ ID NO:4)

TABLE 3-continued

Oligonucleotides used to prepare cDNA fragments corresponding to Dengue virus proteins (by PCR)

2. pMAL-c/NS1-104

DIR2400S     SmaI      NS1
    5' TGG TTC CCG GGG ACT CGG GAT GTG TA
    (SEQ ID NO:5)

DIF3458H    HindIII    NS1
    5'ACT AAG CTT GAT CAT GCA GAG ACC ATT GA
    (SEQ ID NO:6)

3. pMAL-cRI/NS2-1

DIR-NS2PM   EcoRI         NS2
    5'AAT CAG AAT TCT CTG CAG GGT CAG GGG AA
    (SEQ ID NO:7)

DIF-NS2H   HindIII    NS2
    5'ATA ACA AAG CTT ATC TTT GTT TCT TTT TCT
    (SEQ ID NO:8)

4. pGEX-KG/NS3 BHC6001

DIR-NS3B  BamHI      NS3
    5'GAA AGG ATC CTC TGG AGT GTT ATG GGA CAC A
    (SEQ ID NO:9)

DIF-6360H HindIII    NS3
    5'ACC CAA GCT TCA TCT TCT TCC TGC TGC
    (SEQ ID NO:10)

5. pGEX-KG/NS5(C600 HF1)

DIR-75445 SalI        NS5
    5'AGG AGG TCG ACG AGG TAC GGG AGC C
    (SEQ ID NO:11)

DIF-8365
    5'CAA TGA TAT CTA GGT TGG CT
    (SEQ ID NO:12)

TABLE 4

IMMUNE RESPONSES OF MICE AND RABBITS: INDIRECT IMMUNOFLUORESCENCE ASSAYS

| Dengue virus type 1 recombinant proteins | No. of mice | Σ Titrations of IFA |
|---|---|---|
| E | 11 | 14.91 |
| E + CFA | 10 | 39.62 |
| NS1 | 10 | 14.89 |
| NS2 | 10 | 12.05 |
| NS2 + CFA | 10 | 12.07 |
| NS3 | 11 | 10.94 |
| NS3 + CFA | 10 | 42.56 |
| NS5 | 10 | 7.94 |
| NS5 + CFA | 10 | 10.47 |
| E + NS1 | 17 | 16.66 |
| NS3 + NS1 | 18 | 10.87 |
| NS2 + NS3 | 14 | 9.23 |
| NS5 + NS3 | 10 | 32.14 |
| MBP | 4 | <4 |
| GST | 4 | <4 |
| PBS | 2 | <4 |

| Dengue virus type 1 recombinant proteins | No. of rabbits | Σ Titrations of IFA |
|---|---|---|

TABLE 4-continued

IMMUNE RESPONSES OF MICE AND RABBITS: INDIRECT
IMMUNOFLUORESCENCE ASSAYS

| | | |
|---|---|---|
| E | 1 | 160 |
| NS1 | 1 | 160 |
| NS2 (67) | 1 | 2560 |
| NS2 (68) | 1 | 640 |
| NS3 | 1 | 2560 |
| NS5 | 1 | 160 |

We claim:

1. An isolated Dengue viral strain DEN1-S275/90 designated as (E-CACC V92042111).

2. An isolated Dengue viral strain DEN1-S275/90 designated as (ECACC V92042111), in inactivated form.

3. An isolated DNA polynucleotide encoding DEN-1-S275/90 (ECACC V92042111) consisting of the sequence shown in SEQ ID NO:1 or at least one nucleotide sequence selected from the group consisting of nucleic acids 81–422, 123–422, 423–695, 696–920, 921–2402, 2403–3464, 3465–4112, 4113–4499, 4500–6359, 6360–6809, 6810–7556, and 7557–10268, of SEQ ID NO:1.

4. An isolated DNA polynucleotide encoding the polypeptide of SEQ ID NO:2 or at least one amino acid sequence selected from the group consisting of amino acids 1–114, 15–114, 115–205, 206–280, 281–774, 775–1128, 1129–1344, 1345–1474, 1475–2093, 2094–2242, 2243–2492 and 2493–3396 of SEQ ID NO:2.

5. An isolated DNA polynucleotide encoding a fusion protein comprising the polypeptide of SEQ ID NO: 2 or at least one amino acid sequence selected from the group consisting of amino acids 1–114, 15–114, 115–205, 206–280, 281–774, 775–1128, 1129–1344, 1345–1474, 1475–2093, 2094–2242, 2243–2492 and 2493–3396 of SEQ ID NO:2.

6. An expression vector comprising the DNA polynucleotide of any one of claims 3–4.

7. The expression vector according to claim 6, said vector being a plasmid or viral vector.

8. An expression vector comprising the isolated DNA polynucleotide of claim 5.

9. A cell containing the expression vector according to claim 6.

10. The cell according to claim 9, said cell being *E. coli*, a yeast cell or an insect cell.

11. A cell containing the expression vector of claim 8.

12. A method of preparing a polypeptide having an amino acid sequence selected from the group consisting of amino acids 1–114, 15–114, 115–205, 206–280, 281–774, 775–1128, 1129–1344, 1345–1474, 1475–2093, 2094–2242, 2243–2492 and 2493–3396, of SEQ ID NO:2, said method comprising culturing a cell according to claim 9 and recovering said polypeptide.

13. A method of preparing a fusion protein comprising the polypeptide of SEQ ID NO: 2 or at least one amino acid sequence selected from the group consisting of amino acids 1–114, 15–114, 115–205, 206–280, 281–774, 775–1128, 1129–1344, 1345–1474, 1475–2093, 2094–2242, 2243–2492 and 2493–3396 of SEQ ID NO:2, said method comprising culturing a cell according to claim 11 and recovering said fusion protein.

14. A polypeptide in isolated form which is selected from the group consisting of amino acids 1–14, 15–114, 115–205, 206–280, 281–774, 775–1128, 1129–1344, 345–1474, 1475–2093, 2094–2242, 2243–2492 and 2493–3396, of SEQ ID NO:2.

15. An isolated fusion protein comprising the polypeptide according to claim 14.

16. A polypeptide according to claim 14, attached to a label.

17. A fusion protein according to claim 15 attached to a label.

18. A test kit for the detection of the presence or absence of DEN1 virus antibodies comprising a polypeptide according to any one of claims 14–17 fixed to a solid support, said polypeptide being capable of binding antibodies to DEN1-S275/90 (ECACC V92042111).

19. A method of preparing antibodies in an animal, said antibodies being capable of binding a Dengue virus viral protein, said method comprising immunizing said animal with at least one polypeptide according to any one of claims 14–17 or the inactivated virus according to claim 2 and isolating said antibodies.

20. A method as claimed in claim 19 which further comprises in vitro labeling one or more isolated antibodies capable of binding a Dengue viral protein.

21. An isolated antibody prepared according to the method of claim 19.

* * * * *